United States Patent [19]
Kaushansky

[11] Patent Number: 6,099,830
[45] Date of Patent: Aug. 8, 2000

[54] METHODS FOR STIMULATING ERYTHROPOIESIS USING HEMATOPOIETIC PROTEINS

[75] Inventor: Kenneth Kaushansky, Woodinville, Wash.

[73] Assignees: ZymoGenetics, Inc.; University of Washington, both of Seattle, Wash.

[21] Appl. No.: 08/999,927

[22] Filed: Sep. 12, 1997

Related U.S. Application Data

[63] Continuation-in-part of application No. 08/335,566, Nov. 7, 1994, abandoned, which is a continuation-in-part of application No. 08/288,417, Aug. 9, 1994, abandoned.

[51] Int. Cl.$^7$ ............................................. A61K 38/19
[52] U.S. Cl. ............................ 424/85.1; 514/2; 514/8; 514/12; 514/814; 514/885
[58] Field of Search ........................... 514/2, 8, 12, 814, 514/885; 424/84, 85.1

[56] References Cited

U.S. PATENT DOCUMENTS 5,571,686  11/1996  Rosenberg et al. ..................... 435/29

FOREIGN PATENT DOCUMENTS

517925 A1  12/1991  European Pat. Off. .

OTHER PUBLICATIONS

Eaton et al., *Blood 84(10) Suppl. 1*, Abstract No. 948, 241a, 1994.
Broudy et al., *Blood 84(10) Suppl. 1*, Abstract No. 1304, 330a, 1994.
Solberg et al., *Blood 84(10) Suppl. 1*, Abstract No. 1305, 330a, 1994.
Miyazaki et al., *Blood 84(10) Suppl. 1*, Abstract No. 955, 242a, 1994.
de Sauvage et al., *Blood 84(10) Suppl. 1*, Abstract No. 1546, 390a, 1994.
Cases et al., *Kidney International 42*: 668–672, 1992.
Akizawa et al., *Nephron 58*: 400–406, 1991.
Dutton, *Genetic Engineering News*: 8, 1994.
Bartley et al., *Cell 77*: 1117–1124, 1994.
Burstein et al., *Blood Cells 15*: 193–201, 1989.
Farese et al., *Am. Soc. for Blood & Marrow Transplantation Meeting*, Keystone, Colorado, 1995.
Evatt et al., *Blood 48 (4)*: 547–558, 1976.

*Primary Examiner*—Prema Mertz
*Attorney, Agent, or Firm*—Deborah A. Sawislak

[57] ABSTRACT

Methods for stimulating erythropoiesis using the hematopoietic protein thrombopoietin, optionally in combination with erythropoietin, are provided. The methods provided may be used to stimulate erythropoiesis in bone marrow and peripheral blood cells and in vitro and in vivo. In addition, methods for treatment of thrombocytopenia and anemia in patients are disclosed.

14 Claims, 2 Drawing Sheets

METHODS FOR STIMULATING ERYTHROPOIESIS USING HEMATOPOIETIC PROTEINS

CROSS-REFERENCE TO RELATED APPLICATIONS

The present application is a continuation-in-part of Ser. No. 08/335,566 filed on Nov. 7, 1994, which is abandoned, which is a continuation-in-part of Ser. No. 08/288,417 filed on Aug. 9, 1994, which is abandoned, and which are all incorporated herein by reference.

GOVERNMENT SUPPORT

This invention was made with government support under grant numbers CA 31615 and DK43719, awarded by the NIH. The government has certain rights in the inventions.

BACKGROUND OF THE INVENTION

Hematopoiesis is the process by which blood cells develop and differentiate from pluripotent stem cells in the bone marrow. This process involves a complex interplay of polypeptide growth factors (cytokines) acting via membrane-bound receptors on the target cells. Cytokine action results in cellular proliferation and differentiation, with response to a particular cytokine often being lineage-specific and/or stage-specific. Development of a single cell type, such as a platelet or erythrocyte, from a stem cell may require the coordinated action of a plurality of cytokines acting in the proper sequence.

The known cytokines include the interleukins, such as IL-1, IL-2, IL-3, IL-6, IL-8, etc.; and the colony stimulating factors, such as G-CSF, M-CSF, GM-CSF, erythropoietin (EPO), etc. In general, the interleukins act as mediators of immune and inflammatory responses. The colony stimulating factors stimulate the proliferation of marrow-derived cells, activate mature leukocytes, and otherwise form an integral part of the host's response to inflammatory, infectious, and immunologic challenges.

Various cytokines have been developed as therapeutic agents. Several of the colony stimulating factors have been used in conjunction with cancer chemotherapy to speed the recovery of patients' immune systems. Interleukin-2, α-interferon β-interferon and γ-interferon are used in the treatment of certain cancers. EPO, which stimulates the development of erythrocytes, is used in the treatment of anemia arising from renal failure. Factors responsible for stimulation of megakaryocytopoiesis and thrombocytopoiesis resisted definitive characterization, due in part to lack of a good source, a lack of good assays, and a lack of knowledge as to the site(s) of production until recently, despite three decades of work to isolate and characterize them. The megakaryocytopoietic factor referred to in the literature as "thrombopoietin" (recently reviewed by McDonald, *Exp. Hematol.* 16:201–205, 1988; and McDonald, *Am. J. Ped. Hematol. Oncol.* 14:8–21, 1992) has now been identified and isolated (see copending U.S. patent application Ser. No. 08/252,491; Lok et al., *Nature* 369:565–568, 1994; and Kaushansky et al., *Nature* 369:568–571, 1994; all herein incorporated by reference).

Mild bleeding disorders (MBDs) associated with platelet dysfunctions are relatively common (Bachmann, *Seminars in Hematology* 17: 292–305, 1980), as are a number of congenital disorders of platelet function, including Bernard-Soulier syndrome (deficiency in platelet GPIb), Glanzmann's thrombasthenia (deficiency of GPIIb and GPIIIa), congenital afibrinogenemia (diminished or absent levels of fibrinogen in plasma and platelets), and gray platelet syndrome (absence of a-granules). In addition there are a number of disorders associated with platelet secretion, storage pool deficiency, abnormalities in platelet arachidonic acid pathway, deficiencies of platelet cyclooxygenase and thromboxane synthetase and defects in platelet activation (reviewed by Rao and Holmsen, *Seminars in Hematology* 23: 102–118, 1986). At present, the molecular basis for most of these defects is not well understood.

Anemias are deficiencies in the production of red blood cells (erythrocytes) and result in a reduction in the level of oxygen transported by blood to the tissues of the body. Hypoxia may be caused by loss of large amounts of blood through hemorrhage, destruction of red blood cells from exposure to autoantibodies, radiation or chemicals, or reduction in oxygen intake due to high altitudes or prolonged unconsciousness. When hypoxia is present in tissue, EPO production is stimulated and increases red blood cell production. EPO promotes the conversion of primitive precursor cells in the bone marrow into pro-erythrocytes which subsequently mature, synthesize hemoglobin and are released into the circulation as red blood cells. When the number of red blood cells in circulation is greater than needed for normal tissue oxygen requirements, the level of EPO in circulation is decreased.

Severe reductions in both megakaryocyte and erythrocyte levels can be associated with the treatment of various cancers with chemotherapy and radiation and diseases such as AIDS, aplastic anemia and myelodysplasias. Levels of megakaryocytes and/or erythrocytes that become too low, for example, platelet counts below 25,000 to 50,000 and hematocrits of less than 25, are likely to produce considerable morbidity and in certain circumstances these levels are life-threatening. In addition to treating the underlying disease, specific treatments include platelet transfusions for thrombocytopenia (low platelet counts) and stimulation of erythropoiesis using EPO or transfusion of red blood cells for anemia.

Recent advances in molecular biology have greatly increased our understanding of hematopoiesis, but at the same time have shown the process to be extremely complex. While many cytokines have been characterized and some have proven clinical applications, there remains a need in the art for additional agents that stimulate proliferation and differentiation of myeloid and lymphoid precursors and the production of mature blood cells. There is a particular need for agents that stimulate the development and proliferation of cells of the megakaryocytic and erythroid lineages, including platelets and red blood cells. There is a further need in the art for agents that can be used in the simultaneous treatment of cytopenias and anemias such as those caused by destruction of hematopoietic cells in bone marrow such as in the treatment of cancer with chemotherapy and radiation, and pathological conditions such as myelodysplasia, AIDS, aplastic anemia, autoimmune disease or inflammatory conditions. The present invention fulfills these needs and provides other, related advantages.

SUMMARY OF THE INVENTION

It is an object of the present invention to provide methods for stimulating erythropoiesis by culturing bone marrow or peripheral blood cells in the presence of TPO and EPO in an amount sufficient to produce an increase in the number of erythrocytes or erythrocyte precursors as compared to cells cultured without TPO.

It is a further object of the invention to provide methods for stimulating erythropoiesis by culturing bone marrow or peripheral blood cells in the presence of a composition comprising TPO in an amount sufficient to produce an increase in the number of erythrocytes or erythrocyte precursors as compared to cells cultured without TPO.

It is a further object of the invention to provide methods for stimulating erythropoiesis in a mammal by administering a composition comprising TPO in a pharmaceutically acceptable vehicle to produce an increase in proliferation or differentiation of erythroid cells.

It is a further object of the invention to provide methods for stimulating erythropoiesis in a mammal by administering a composition comprising EPO and TPO in a pharmaceutically acceptable vehicle to produce an increase in proliferation or differentiation of erythroid cells.

It is a further object of the invention to provide methods for stimulating erythropoiesis in a patient by administering a composition comprising EPO and TPO in amount sufficient to increase reticulocyte counts and erythroid colony formation.

It is a further object of the invention to provide methods for stimulating erythropoiesis in a patient by administering a composition comprising TPO in an amount sufficient for increasing reticulocyte counts at least 2-fold over baseline reticulocyte counts.

It is a further object of the invention to provide methods for stimulating erythropoiesis in a patient by administering a composition comprising TPO and EPO in an amount sufficient for increasing reticulocyte counts at least 2-fold over baseline reticulocyte counts.

Within one aspect, the present invention provides that the TPO is human TPO. In another embodiment, the TPO comprises a sequence of amino acids selected from group consisting of: the sequence of amino acids shown in SEQ ID NO:2 from amino acid residue 1 to residue 172; the sequence of amino acids shown in SEQ ID NO:2 from amino acid residue 1 to residue 173; the sequence of amino acids shown in SEQ ID NO:2 from amino acid residue 1 to residue 175; the sequence of amino acids shown in SEQ ID NO:2 from amino acid residue 1 to amino acid residue 353; the sequence of amino acids shown in SEQ ID NO:2 from amino acid residue 22 to residue 353; the sequence of amino acids shown in SEQ ID NO:2 from amino acid residue 22 to residue 172; the sequence of amino acids shown in SEQ ID NO:2 from amino acid residue 22 to residue 173; the sequence of amino acids shown in SEQ ID NO:2 from amino acid residue 22 to residue 175; the sequence of amino acids shown in SEQ ID NO:2 from amino acid residue 28 to residue 172; the sequence of amino acids shown in SEQ ID NO:2 from amino acid residue 28 to residue 173; the sequence of amino acids shown in SEQ ID NO:2 from amino acid residue 28 to residue 175; and the sequence of amino acids shown in SEQ ID NO:2 from amino acid residue 28 to residue 353.

Within another aspect, the invention provides methods where a mammal is administered TPO at $1.0 \times 10^5$ to $100 \times 10^5$ units TPQ/kg/day, preferably $1.0 \times 10^5$ to $25 \times 10^5$ units TPQ/kg/day.

In another embodiment, the invention provides methods where a mammal is administered a combination of TPO at $1.0 \times 10^5$ to $100 \times 10^5$ units TPO/kg/day, preferably $1.0 \times 10^5$ to $25 \times 10^5$ units TPQ/kg/day, and EPO at 1 to 150 units EPO/kg/day.

DETAILED DESCRIPTION OF THE INVENTION

Figure 1:
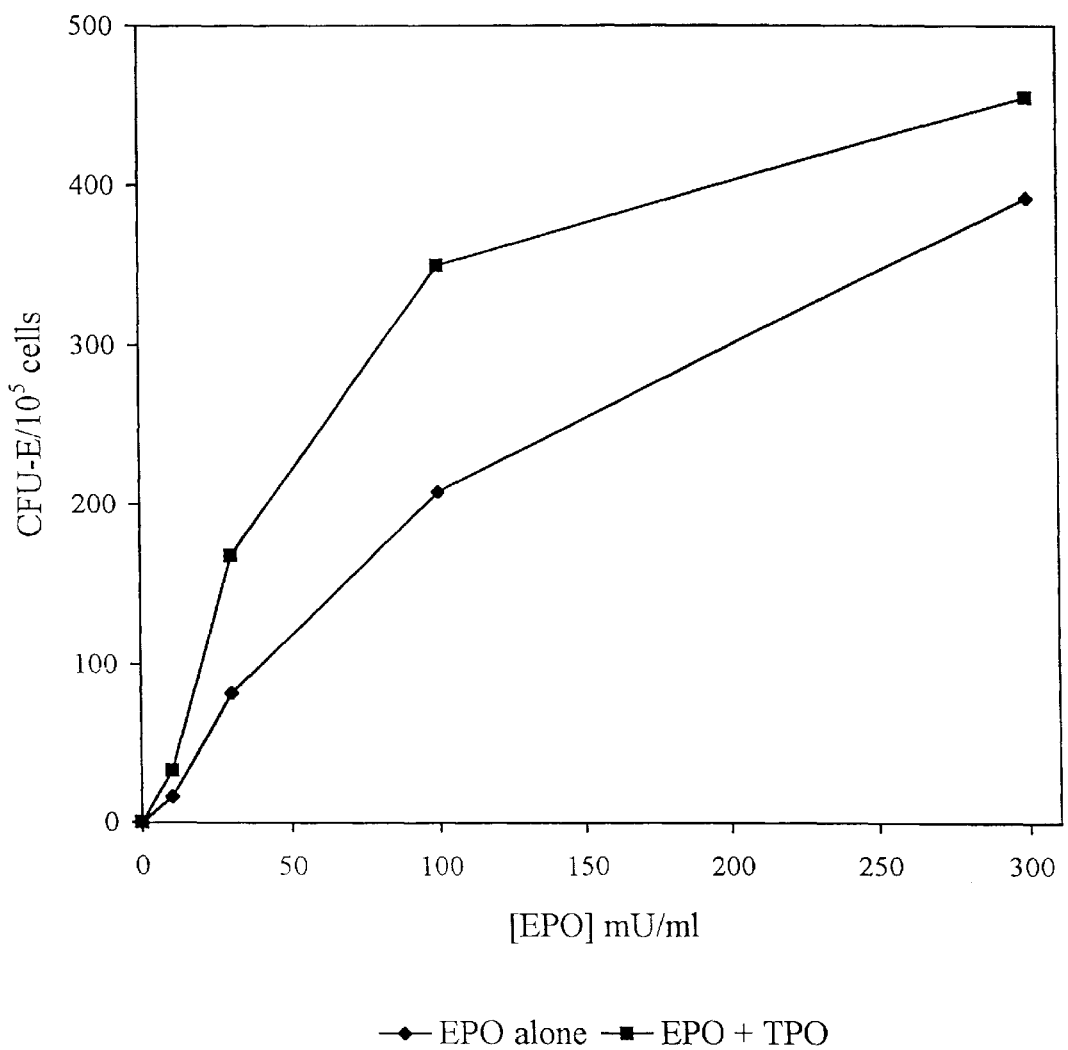
FIG. 1 illustrates that following the addition of TPQ and EPO to cultured bone marrow cells, erythroid colony formation is enhanced relative to addition of EPO alone.

Prior to describing the present invention in detail, it may be helpful to define certain terms used herein:

Allelic variant: An alternative form of a gene that arises through mutation, or an altered polypeptide encoded by the mutated gene. Gene mutations can be silent (no change in the encoded polypeptide) or may encode polypeptides having altered amino acid sequence.

cDNA: Complementary DNA, prepared by reverse transcription of a messenger RNA template, or a clone or amplified copy of such a molecule. Complementary DNA can be single-stranded or double-stranded.

Expression vector: A DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both. The term "operably linked" indicates that the segments are arranged so that they function in concert for their intended purposes, e.g. transcription initiates in the promoter and proceeds through the coding segment to the terminator.

Gene: A segment of chromosomal DNA that encodes a polypeptide chain. A gene includes one or more regions encoding amino acids, which in some cases are interspersed with non-coding "intervening sequences" ("introns"), together with flanking, non-coding regions which provide for transcription of the coding sequence.

Molecules complementary to: Polynucleotide molecules having a complementary base sequence and reverse orientation as compared to a reference sequence. For example, the sequence 5' ATGCACGGG 3' is complementary to 5° CCCGTGCAT 3'.

Promoter: The portion of a gene at which RNA polymerase binds and mRNA synthesis is initiated.

As noted above, the present invention provides methods for stimulating thrombopoiesis and erythropoiesis using proteins having hematopoietic activity. As used herein, the term "hematopoietic" denotes the ability to stimulate the proliferation and/or differentiation of myeloid or lymphoid precursors as determined by standard assays. See, for example, Metcalf, *Proc. Natl. Acad. Sci. USA* 77: 5327–5330, 1980; Metcalf et al., *J. Cell. Physiol.* 116: 198–206, 1983; and Metcalf et al., *Exp. Hematol.* 15: 288–295, 1987. Typically, marrow cells are incubated in the presence of a test sample and a control sample. The cultures are then scored for cell proliferation and differentiation by visual examination and/or staining. A particularly preferred assay is the MTT calorimetric assay of Mosman (*J. Immunol. Meth.* 65: 55–63, 1983; incorporated herein by reference).

As used herein, the term "erythropoiesis" denotes the proliferation and/or differentiation of erythroid precursor cells. Standard measures of erythroid cell proliferation and differentiation include hematocrit and reticulocyte counts. Hematocrit is a measurement of red blood cells, and is commonly expressed as the percentage of total blood volume which consists of erythrocytes. Reticulocyte counts measure 1–2 day-old cells that contain mRNA (absent in mature erythrocytes) and aggregates of ribosomes as demonstrated by staining (Erslev, A., "Reticulocyte Enumeration", in *Hematology*, McGraw-Hill, NY, 1990). A reticulocyte count is the percentage of such cells per 500 or 1000 cells counted. An average range for reticulocyte counts is 0.8% to 1.2%. EPO is commercially available (R & D Systems, Minneapolis, Minn. and Amgen, Thousand Oaks, Calif.) and activity is measured by calibration against the second international reference preparation of erythropoietin (Annable et al., *Bull. Wld. Hlth. Org.* 47:99, 1972) using an in vivo assay which measures the incorporation of $^{56}$Fe into red blood cells of exhypoxic polycythemic mice (Cotes et al., *Nature* 191:1065, 1961) or by in vitro cell proliferation assay that uses a factor-dependent human erythroleukemic cell line, TF-1 (Kitamura et al., *J. Cell. Physiol.* 140:323, 1989).

The present invention is based in part upon the discovery that thrombopoietin (TPO) stimulates erythroid cell growth. When the present inventors administered TPO to thrombocytopenic mammals, in addition to an increase in platelets, surprisingly TPO was found to augment the recovery of red blood cells and produce a rapid increase in hematocrit levels.

The sequences of cDNA clones encoding representative human and mouse TPO proteins are shown in SEQ ID NO: 1 and SEQ ID NO: 3, respectively, and the corresponding amino acid sequences are shown in SEQ ID NO: 2 and SEQ ID NO: 4, respectively. Those skilled in the art will recognize that the sequences shown in SEQ ID NOS: 1, 2, 3 and 4 and the human genomic sequence shown in SEQ ID NOS: 5 and 6, correspond to single alleles of the human gene, and that allelic variation is expected to exist. It will also be evident that one skilled in the art could engineer sites that would facilitate manipulation of the nucleotide sequence using alternative codons.

The present invention provides methods for stimulating erythropoiesis using proteins that are substantially homologous to the proteins of SEQ ID NO: 2 and their species homologs. By "isolated" is meant a protein which is found in a condition other than its native environment, such as apart from blood and animal tissue. In a preferred form, the isolated protein is substantially free of other proteins, particularly other proteins of animal origin. It is preferred to provide the proteins in a highly purified form, i.e. greater than 95% pure, more preferably greater than 99% pure. The term "substantially homologous" is used herein to denote proteins having 50%, preferably 60%, more preferably at least 80%, sequence identity to the sequences shown in SEQ ID NO: 2 or their species homologs. Such proteins will more preferably be at least 90% identical, and most preferably 95% or more identical to SEQ ID NO: 2 or their species homologs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 1 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Substantially homologous proteins are characterized as having one or more amino acid substitutions, deletions or additions. These changes are preferably of a minor nature, that is conservative amino acid substitutions that do not significantly affect the folding or activity of the protein (see Table 2); small deletions, typically of one to about 30 amino acids; and small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. See, in general Ford et al., *Protein Expression and Purification* 2: 95–107, 1991, which is incorporated herein by reference.

TABLE 2

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Essential amino acids in TPO and EPO may be identified according to procedures known in the art, such as site-directed mutagenesis or alanine-scanning mutagenesis (Cunningham and Wells, Science 244, 1081–1085, 1989). In the latter technique, single alanine mutations are introduced at every residue in the molecule, and the resultant mutant molecules are tested for biological activity (e.g. receptor binding, in vitro or in vivo proliferative activity) to identify amino acid residues that are critical to the activity of the molecule. Sites of ligand-receptor interaction can also be determined by analysis of crystal structure as determined by such techniques as nuclear magnetic resonance, crystallography or photoaffinity labeling. See, for example, de Vos et al., Science 255:306–312, 1992; Smith et al., J. Mol. Biol. 224:899–904, 1992; Wlodaver et al., FEBS Lett. 309:59–64, 1992.

Biologically active muteins of EPO based on elucidation of structure-function relationships have recently been identified (Boissel et al., J. of Biol. Chem. 268:15983–15993, 1993 and Higuchi et al., J. Biol. Chem. 267:7703–7709, 1992). EPO isoforms having different sialic acid compositions are disclosed by Strickland et al. EP 0428267.

In general, cytokines are predicted to have a four-alpha helix structure, with the first and fourth helices being most important in ligand-receptor interactions and more highly conserved among members of the family. Referring to the human TPO amino acid sequence shown in SEQ ID NO: 2, alignment of cytokine sequences suggests that these helices are bounded by amino acid residues 29 and 53, 80 and 99, 108 and 130, and 144 and 168, respectively (boundaries are ±4 residues). Helix boundaries of the mouse and other non-human TPOs can be determined by alignment with the human sequence. Other important structural aspects of TPO include the cysteine residues at positions 28, 50, 106 and 172 of SEQ ID NO: 2.

In addition to the hematopoietic proteins disclosed above, the methods of the present invention include utilization of fragments of these proteins and isolated polynucleotide molecules encoding the fragments. Of particular interest are fragments of at least 10 amino acids in length that bind to an MPL receptor, and polynucleotide molecules of at least 30 nucleotides in length encoding such polypeptides. Polypeptides of this type are identified by known screening methods, such as by digesting the intact protein or synthesizing small, overlapping polypeptides or polynucleotides (and expressing the latter), optionally in combination with the techniques of structural analysis disclosed above. The resultant polypeptides are then tested for the ability to specifically bind the MPL receptor and stimulate cell proliferation via the MPL receptor. Binding is determined by conventional methods, such as that disclosed by Klotz, Science 217: 1247, 1982 ("Scatchard analysis"). Briefly, a radiolabeled test polypeptide is incubated with MPL receptor-bearing cells in the presence of increasing concentrations of unlabeled TPO. Cell-bound, labeled polypeptide is separated from free labeled polypeptide by centrifugation through phthalate oil. The binding affinity of the test polypeptide is determined by plotting the ratio of bound to free label on the ordinate versus bound label on the abscissa. Binding specificity is determined by competition with cytokines other than TPO. Receptor binding can also be determined by precipitation of the test compound by immobilized MPL receptor (or the ligand-binding extracellular domain thereof). Briefly, the receptor or portion thereof is immobilized on an insoluble support. The test compound is labeled, e.g. by metabolically labeling of the host cells in the case of a recombinant test compound, or by conventional, in vitro labeling methods (e.g. radio-iodination). The labeled compound is then combined with the immobilized receptor, unbound material is removed, and bound, labeled compound is detected. Methods for detecting a variety of labels are known in the art. Stimulation of proliferation is conveniently determined using the MTT calorimetric or $^3$H-thymidine incorporation assay with MPL receptor-bearing cells. Polypeptides are assayed for activity at various concentrations, typically over a range of 1 nm to 1 mM.

Larger polypeptides of up to 50 or more residues, preferably 100 or more residues, more preferably about 140 or more residues, up to the size of the entire mature protein are also provided. For example, analysis and modeling of the amino acid sequence shown in SEQ ID NO:2 from residue 28 to residue 172, inclusive, suggest that this portion of the molecule is a cytokine-like domain capable of self assembly. Also of interest are molecules containing this core cytokine-like domain plus one or more additional segments or domains of the primary translation product. Thus, other polypeptides of interest include those shown in Table 3.

TABLE 3

Mouse TPO (SEQ ID NO:4)

Cys (residue 51)--Cys (residue 195)
Cys (51)--Val (196)
Cys (51)--Pro (206)
Cys (51)--Ser (207)
Cys (51)--Asn (216)
Cys (51)--Arg (235)
Cys (51)--Arg (244)
Cys (51)--Arg (249)
Cys (51)--Gln (259)
Cys (51)--Arg (273)
Ser (45)--Cys (195)
Ser (45)--Val (196)
Ser (45)--Pro (206)
Ser (45)--Ser (207)
Ser (45)--Asn (216)
Ser (45)--Arg (235)
Ser (45)--Arg (244)
Ser (45)--Arg (249)
Ser (45)--Gln (259)
Ser (45)--Arg (273)

Human TPO (SEQ ID NO:2)

Cys (28)--Cys (172)
Cys (28)--Val (173)
Cys (28)--Arg (175)
Cys (28)--Arg (185)
Cys (28)--Asn (193)

TABLE 3-continued

Cys (28)--Arg (198)
Cys (28)--Phe (207)
Cys (28)--Gln (235)
Cys (28)--Arg (266)
Ser (22)--Cys (172)
Ser (22)--Val (173)
Ser (22)--Arg (175)
Ser (22)--Arg (185)
Ser (22)--Asn (193)
Ser (22)--Arg (198)
Ser (22)--Phe (207)
Ser (22)--Gln (235)
Ser (22)--Arg (266)

Those skilled in the art will recognize that intermediate forms of the molecules (e.g. those having C-termini between residues 196 and 206 of SEQ ID NO: 4 between residues 185 and 193 of SEQ ID NO: 2 or those having N-termini between residues 22 and 28 of SEQ ID NO: 2) are also of interest, as are polypeptides having one or more amino acid substitutions, deletions, insertions, or N- or C-terminal extensions as disclosed above. Thus, the present invention provides hematopoietic polypeptides of at least 10 amino acid residues, preferably at least 50 residues, more preferably at least 100 residues and most preferably at least about 140 residues in length, wherein said polypeptides are substantially homologous to like-size polypeptides of SEQ ID NO:2.

The proteins used in the present invention for stimulating erythropoiesis can be produced in genetically engineered host cells according to conventional techniques. Suitable host cells are those cell types that can be transformed or transfected with exogenous DNA and grown in culture, and include bacteria, fungal cells, and cultured higher eukaryotic cells. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., ibid., which are incorporated herein by reference. Production of recombinant EPO has been described in Lin et al., EP 014805; Fritsch et al., EP 0411678; Fritsch et al., EP 0205564; Hegwick et al., EP 0209539; Lin et al., WO 85/02610; U.S. Pat. No. 4,677,195 and U.S. Pat. No. 4,703,008. Production of recombinant TPO has been described in Lok et al. *Nature* 369:565–568, 1994; Bartley et al., *Cell* 77:1117–1124, 1994 and Sauvage et al., *Nature* 369:533–538, 1994.

In general, a DNA sequence encoding a cytokine is operably linked to a transcription promoter and terminator within an expression vector. The vector will commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a protein into the secretory pathway of the host cells, a secretory signal sequence (also known as a leader sequence, prepro sequence or pre sequence) is provided in the expression vector. The secretory signal sequence is joined to the DNA sequence encoding a protein of interest in the correct reading frame. Secretory signal sequences are commonly positioned 5' to the DNA sequence encoding the protein of interest, although certain signal sequences may be positioned elsewhere in the DNA sequence of interest (see, e.g., Welch et al., U.S. Pat. No. 5,037,743; Holland et al., U.S. Pat. No. 5,143,830). The secretory signal sequence may be that normally associated with a protein of interest, or may be from a gene encoding another secreted protein.

Yeast cells, particularly cells of the genus Saccharomyces, are a preferred host for producing cytokines for use within the present invention. Methods for transforming yeast cells with exogenous DNA and producing recombinant proteins therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075, which are incorporated herein by reference. Transformed cells are selected by phenotype determined by the selectable marker, commonly drug resistance or the ability to grow in the absence of a particular nutrient (e.g. leucine). A preferred vector system for use in yeast is the POT1 vector system disclosed by Kawasaki et al. (U.S. Pat. No. 4,931,373), which allows transformed cells to be selected by growth in glucose-containing media. A preferred secretory signal sequence for use in yeast is that of the *S. cerevisiae* MFa1 gene (Brake, ibid.; Kurjan et al., U.S. Pat. No. 4,546,082). Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092, which are incorporated herein by reference) and alcohol dehydrogenase genes. See also U.S. Pat. Nos. 4,990,446; 5,063,154; 5,139,936 and 4,661,454, which are incorporated herein by reference. Transformation systems for other yeasts, including *Hansenula polymorpha, Schizosaccharomyces pombe, Kluyveromyces lactis, Kluyveromyces fragilis, Ustilago maydis, Pichia pastoris, Pichia guillermondii* and *Candida maltosa* are known in the art. See, for example, Gleeson et al., *J. Gen. Microbiol.* 132:3459–3465, 1986 and Cregg, U.S. Pat. No. 4,882,279.

Other fungal cells are also suitable as host cells. For example, Aspergillus cells may be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference. Methods for transforming Neurospora are disclosed by Lambowitz, U.S. Pat. No. 4,486,533, which is incorporated herein by reference.

Cultured mammalian cells are also preferred hosts. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982) and DEAE-dextran mediated transfection (Ausubel et al., eds., *Current Protocols in Molecular Biology*, John Wiley and Sons, Inc., NY, 1987), which are incorporated herein by reference. The production of recombinant proteins in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen.*

Virol. 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978, which are incorporated herein by reference) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. Transformation of insect cells and production of foreign proteins therein is disclosed by Guarino et al., U.S. Pat. No. 5,162,222; Bang et al., U.S. Pat. No. 4,775,624; and WIPO publication WO 94/06463, which are incorporated herein by reference. The use of Agrobacterium rhizogenes as a vector for expressing genes in plant cells has been reviewed by Sinkar et al., *J. Biosci. (Bangalore)* 11:47–58, 1987.

Preferred prokaryotic host cells are strains of the bacteria *Escherichia coli*, although Bacillus and other genera are also useful. Techniques for transforming these hosts and expressing foreign DNA sequences cloned therein are well known in the art (see, e.g., Sambrook et al., ibid.). When expressing the proteins in bacteria such as *E. coli*, the protein may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate. The denatured protein is then refolded by diluting the denaturant. In the latter case, the protein can be recovered from the periplasmic space in a soluble and functional form by disrupting the cells (by, for example, sonication or osmotic shock) to release the contents of the periplasmic space and recovering the protein.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Transgenic animal technology may be employed to produce TPO and EPO for use in the present invention. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and well characterized biochemically. Furthermore, the major milk proteins are present in milk at high concentrations (from about 1 to 15 g/l).

From a commercial point of view, it is clearly preferable to use as the host a species that has a large milk yield. While smaller animals such as mice and rats can be used (and are preferred at the proof-of-concept stage), it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk. See WIPO Publication WO 88/00239 for a comparison of factors influencing the choice of host species. It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489, incorporated herein by reference), beta-lactoglobulin, a-lactalbumin, and whey acidic protein. The beta-lactoglobulin (BLG) promoter is preferred. In the case of the ovine beta-lactoglobulin gene, a region of at least the proximal 406 bp of 5' flanking sequence of the gene will generally be used, although larger portions of the 5' flanking sequence, up to about 5 kbp, are preferred, such as a ~4.25 kbp DNA segment encompassing the 5' flanking promoter and non-coding portion of the beta-lactoglobulin gene. See Whitelaw et al., *Biochem J.* 286: 31–39, 1992. Similar fragments of promoter DNA from other species are also suitable.

Other regions of the beta-lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., *Proc. Natl. Acad. Sci. USA* 85: 836–840, 1988; Palmiter et al., *Proc. Natl. Acad. Sci. USA* 88: 478–482, 1991; Whitelaw et al., *Transgenic Res.* 1: 3–13, 1991; WO 89/01343; WO 91/02318). In this regard, it is generally preferred, where possible, to use genomic sequences containing all or some of the native introns of a gene encoding the protein or polypeptide of interest, thus the further inclusion of at least some introns from, e.g, the beta-lactoglobulin gene, is preferred. One such region is a DNA segment which provides for intron splicing and RNA polyadenylation from the 3' non-coding region of the ovine beta-lactoglobulin gene. When substituted for the natural 3' non-coding sequences of a gene, this ovine beta-lactoglobulin segment can both enhance and stabilize expression levels of the protein or polypeptide of interest. Within other embodiments, the region surrounding the initiation ATG of the cytokine sequence is replaced with corresponding sequences from a milk specific protein gene. Such replacement provides a putative tissue-specific initiation environment to enhance expression. It is convenient to replace the entire cytokine pre-pro and 5' non-coding sequences with those of, for example, the BLG gene, although smaller regions may be replaced.

For expression of cytokines in transgenic animals, a DNA segment encoding the cytokine is operably linked to additional DNA segments required for its expression to produce expression units. Such additional segments include the above-mentioned promoter, as well as sequences which provide for termination of transcription and polyadenylation of mRNA. The expression units will further include a DNA segment encoding a secretory signal sequence operably linked to the segment encoding the cytokine. The secretory signal sequence may be a native cytokine secretory signal sequence or may be that of another protein, such as a milk protein. See, for example, von Heinje, *Nuc. Acids Res.* 14: 4683–4690, 1986; and Meade et al., U.S. Pat. No. 4,873,316, which are incorporated herein by reference.

Construction of expression units for use in transgenic animals is conveniently carried out by inserting a cytokine-encoding sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of the cytokine of interest, thereby creating a gene fusion that includes the expression control sequences of the milk protein gene. In any event, cloning of the expression units in plasmids or other vectors facilitates the amplification of the cytokine sequence. Amplification is conveniently carried out in bacterial (e.g. *E. coli*) host cells, thus the vectors will typically include an origin of replication and a selectable marker functional in bacterial host cells.

The expression unit is then introduced into fertilized eggs (including early-stage embryos) of the chosen host species. Introduction of heterologous DNA can be accomplished by one of several routes, including microinjection (e.g. U.S. Pat. No. 4,873,191), retroviral infection (Jaenisch, *Science* 240: 1468–1474, 1988) or site-directed integration using embryonic stem (ES) cells (reviewed by Bradley et al., *Bio/Technology* 10: 534–539, 1992). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds.

General procedures for producing transgenic animals are known in the art. See, for example, Hogan et al., *Manipulating the Mouse Embryo: A Laboratory Manual*, Cold Spring Harbor Laboratory, 1986; Simons et al., *Bio/Technology* 6: 179–183, 1988; Wall et al., *Biol. Reprod.* 32: 645–651, 1985; Buhler et al., *Bio/Technology* 8: 140–143, 1990; Ebert et al., *Bio/Technology* 9: 835–838, 1991; Krimpenfort et al., *Bio/Technoloqy* 9: 844–847, 1991; Wall et al., *J. Cell. Biochem.* 49: 113–120, 1992; U.S. Pat. Nos. 4,873,191 and 4,873,316; WIPO publications WO 88/00239, WO 90/05188, WO 92/11757; and GB 87/00458, which are incorporated herein by reference. Techniques for introducing foreign DNA sequences into mammals and their germ cells were originally developed in the mouse. See, e.g., Gordon et al., *Proc. Natl. Acad. Sci. USA* 77: 7380–7384, 1980; Gordon and Ruddle, *Science* 214: 1244–1246, 1981; Palmiter and Brinster, *Cell* 41: 343–345, 1985; Brinster et al., *Proc. Natl. Acad. Sci. USA* 82: 4438–4442, 1985; and Hogan et al. (ibid.). These techniques were subsequently adapted for use with larger animals, including livestock species (see e.g., WIPO publications WO 88/00239, WO 90/05188, and Wo 92/11757; and Simons et al., *Bio/Technology* 6: 179–183, 1988). To summarize, in the most efficient route used to date in the generation of transgenic mice or livestock, several hundred linear molecules of the DNA of interest are injected into one of the pro-nuclei of a fertilized egg according to techniques which have become standard in the art. Injection of DNA into the cytoplasm of a zygote can also be employed.

Production in transgenic plants may also be employed. Expression may be generalized or directed to a particular organ, such as a tuber. See, Hiatt, *Nature* 344:469–479, 1990; Edelbaum et al., *J. Interferon Res.* 12:449–453, 1992; Sijmons et al., *Bio/Technology* 8:217–221, 1990; and European Patent Office Publication EP 255,378.

TPO and EPO are purified using methods generally known in the art, such as affinity purification and separations based on size, charge, solubility and other properties of the protein. When the protein is produced in cultured mammalian cells, it is preferred to culture the cells in a serum-free culture medium in order to limit the amount of contaminating protein. The medium is harvested and fractionated. Preferred methods of fractionation include affinity chromatography on concanavalin A or other lectin, thereby making use of the carbohydrate present on the protein. TPO can also be purified using an immobilized MPL receptor protein or ligand-binding portion thereof or through the use of an affinity tag (e.g. polyhistidine, substance P or other polypeptide or protein for which an antibody or other specific binding agent is available). A specific cleavage site may be provided between the protein of interest and the affinity tag. EPO has been purified from uremic patients exhibiting elevated EPO levels, see U.S. Pat. Nos. 4,397,840, 4,303,650 and 3,865,801 and Miyake et al. *J. Biol. Chem.* 252:5558, 1977. EPO obtained from both uremic patients and recombinant methods have been purified using reverse-phase HPLC (Hewick et al. U.S. Pat. No. 4,677,195).

TPO proteins can be used therapeutically wherever it is desirable to increase proliferation of hematopoietic cells in the bone marrow, such as in the treatment of cytopenia and anemia, such as that induced by aplastic anemia, myelodysplastic syndromes, autoimmune diseases, AIDS, chemotherapy or radiation.

Compositions containing TPO will have useful application in the treatment of disorders characterized by low red blood cell production (anemia), particularly when accompanied by low platelet production (thrombocytopenia). Various chemotherapeutic treatments of cancers and disease states are known to result in a combination of low platelet and erythrocyte levels in patients.

Compositions of TPO have been found effective for increasing the level of circulating erythrocytes and erythrocyte precursor cells. Reduction in the circulating levels of these cells is known as anemia. The erythrocyte level in blood is measured as the amount of hemoglobin per 100 ml or as the volume of packed red blood cells per 100 ml of blood. Patients are diagnosed as anemic if their hemoglobin levels fall below 11–13 gm/100 ml of blood (depending upon the age and sex of the patient). The methods of the present invention are particularly useful for treatment of anemias associated with bone marrow failure, where a decrease in blood cell formation is associated with, for example, the toxic effects of chemotherapy.

TPO proteins have been found useful for simultaneous treatment of thrombocytopenia and anemia by increasing platelet production with a concurrent increase in erythroid cell levels. Anemia and thrombocytopenia are associated with a diverse group of diseases and clinical situations that may act alone or in concert to produce the condition.

Lowered platelet counts may be associated with anemia, for example, by dilutional losses due to massive transfusions, or abnormal destruction of bone marrow. For example, chemotherapeutic drugs used in cancer therapy may suppress development of platelet and erythroid progenitor cells in the bone marrow, and the resulting thrombocytopenia and anemia limit the chemotherapy and may necessitate transfusions. In addition, certain malignancies can impair platelet and erythrocyte production and distribution. Radiation therapy used to kill malignant cells also kills platelet and erythroid progenitor cells. Abnormal destruction of platelets and erythrocytes can result from hematologic disorders such as leukemia and lymphoma or metastatic cancers involving bone marrow. Other indications for the use of TPO to treat concurrent anemia and thrombocytopenia include aplastic anemia and drug-induced marrow suppression resulting from, for example, chemotherapy or treatment of HIV infection with AZT.

Thrombocytopenia is manifested as increased bleeding, such as mucosal bleedings from the nasal-oral area or the gastrointestinal tract, as well as oozing from wounds, ulcers or injection sites. Symptoms of anemia include dyspnea with exertion, dizziness, fatigue, and pallor of the skin and mucous membranes. When associated with thrombocytopenia, retinal hemorrhage can be present.

EPO has been used for stimulating erythrocyte production. EPO is a an acidic glycoprotein of approximately 34,000 dalton molecular weight and may occur in three forms: a, b, and asialo. The a and b forms differ slightly in carbohydrate components, but have the same potency, biological activity and molecular weight. The asialo form is an a or b form with the terminal carbohydrate (sialic acid) removed. Erythropoietin is present in very low concentrations in plasma when the body is in a healthy state and tissues are receiving sufficient oxygenation from the existing number of erythrocytes. See, for example, Lin et al., U.S. Pat. No. 4,703,008; Lin et al., WO 85/02610; Fritsch et al. EP 0411678; Hewick et al., EP 0209539 and Hewick et al., U.S. Pat. No. 4,677,195, which are incorporated herein by reference.

In normal individuals, red blood cell production is precisely controlled to sufficiently oxygenate tissue without producing an overabundance of red blood cells and impeding circulation. A reduction in red blood cell production, resulting in tissue hypoxia, stimulates EPO expression and increases endogenous EPO found in plasma. EPO increases red blood cell production by stimulating the conversion of primitive precursor cells in the bone marrow into pro-erythroblasts which subsequently mature, synthesize hemoglobin and are released into the circulation as red blood cells.

To provide for the stimulatory effect of TPO and EPO for erythropoiesis, the present invention does not always require the administration of exogenous EPO. As stated previously, a reduction in the level of red blood cells will in some cases result in an elevation in the endogenous levels of EPO (greater than 500 mU/ml of plasma) and administration of TPO alone may be sufficient. In cases where expression of erythropoietin is not elevated, then erythropoietin is advantageously administered with compositions of TPO.

As a therapeutic, EPO is administered to uremic patients where the hemoglobin concentration is less than 10 gm/100 ml of blood. The route of administration can be either intravenous (IV) or subcutaneous (SC), and frequency varies from daily to weekly depending upon the patient's physical condition (De Marchi et al. *Clin. and Experim. Rheumatol.* 11:429–444, 1993; Miller et al., *N. Eng. J. of Med.* 322:1689–1692, 1990; Nissenson et al., *Annals of Int. Med.* 114:402–416, 1991; Erslev, *Sem. Oncol.* 19(8) *Suppl.* 8:14–18, 1992 and PROCIT Epotin-alfa package insert, Amgen, Thousand Oaks, Calif.).

For pharmaceutical use, TPO and EPO are formulated for parenteral, particularly intravenous or subcutaneous, delivery according to conventional methods. Intravenous administration will be by bolus injection or infusion over a typical period of one to several hours. In general, pharmaceutical formulations will include the hematopoietic proteins in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. In addition, TPO and EPO may be combined with other cytokines, particularly early-acting cytokines such as stem cell factor, IL-3, IL-6, IL-11 or GM-CSF. When utilizing such a combination therapy, the cytokines may be combined in a single formulation or may be administered in separate formulations. Methods of formulation are well known in the art and are disclosed, for example, in *Remington's Pharmaceutical Sciences*, Gennaro, ed., Mack Publishing Co., Easton Pa., 1990, which is incorporated herein by reference. Therapeutic doses of TPO will generally be in the range of $1.0 \times 10^5$ to $100 \times 10^5$ units/kg of patient weight per day, preferably $1.0 \times 10^5$ to $25 \times 10^5$ units/kg per day based on an in vitro mitogenesis assay of >95% pure protein. (Those skilled in the art will recognize that results of in vitro assays using cultured cells will routinely vary over a range of ±20%). These doses correspond to approximately 1.2 μg/kg/day to 114 μg/kg/day, preferably 1.2 lg/kg/day to 50 lg/kg/day. In some instances, lower ranges may be appropriate, when, for example, patients show increased sensitivity or require prolonged treatment. In such cases a range of $0.1 \times 10^5$ to $50 \times 10^5$ units TPO/kg/day, preferably $0.5 \times 10^5$ to $25 \times 10^5$ units TPO/kg/day, will be beneficial. Therapeutic doses of EPO will generally be in the range of 10–150 U/kg of patient weight per day, preferably 50–150 U/kg per day. For both TPO and EPO, the exact dose will be determined by the clinician according to accepted standards, taking into account the nature and severity of the condition to be treated, patient traits, etc. Determination of dose is within the level of ordinary skill in the art. The proteins will commonly be administered over a period of up to 28 days following chemotherapy, radiation therapy or bone-marrow transplant or until a platelet count of >20,000/mm$^3$, preferably >50,000/mm$^3$, a hematocrit of 30–33% and reticulocyte counts that are at least 2-fold over baseline are achieved. More commonly, the proteins will be administered over one week or more, often over a period of seven to fourteen days. In general, a therapeutically effective amount of TPO or EPO is an amount sufficient to produce a clinically significant increase in the proliferation and/or differentiation of lymphoid or myeloid progenitor cells, which will be manifested as an increase in circulating levels of mature cells (e.g. platelets or erythrocytes). Treatment of platelet disorders will thus be continued until a platelet count of at least 20,000/mm$^3$, preferably 50,000/mm$^3$, is reached. Treatment of anemias will continue until hematocrit levels of 30–33% and a reticulocyte count of at least 2-fold over baseline, a level that is adequate to have a significant impact upon hematocrit, are reached. As stated previously, a normal range for reticulocyte counts is 0.8% to 1.2%. TPO and EPO can also be administered in combination with other cytokines such as IL-3,–6 and -11; stem cell factor; G-CSF and GM-CSF. Within regimens of combination therapy, daily doses of other cytokines will in general be: GM-CSF, 5–15 μg/kg; IL-3, 1–5 lg/kg; and G-CSF, 1–25 μg/kg. Combination therapy with GM-CSF, for example, is indicated in patients with low neutrophil levels.

TPO and EPO can also be used ex vivo, such as in autologous marrow culture. Briefly, bone marrow is removed from a patient prior to chemotherapy and treated with TPO, optionally in combination with EPO, optionally in combination with one or more additional cytokines. The treated marrow is then returned to the patient after chemotherapy to speed the recovery of the marrow. In addition, TPO, alone and in combination with EPO, can also be used for the ex vivo expansion of marrow or peripheral blood progenitor (PBPC) cells. Prior to chemotherapy treatment, marrow can be stimulated with stem cell factor (SCF) or G-CSF to release early progenitor cells into peripheral circulation. These progenitors can be collected and concentrated from peripheral blood and then treated in culture with TPO and EPO, optionally in combination with one or more other cytokines, including but not limited to SCF, G-CSF, IL-3, GM-CSF, IL-6 or IL-11, to differentiate and proliferate into high-density megakaryocyte cultures, which can then be returned to the patient following high-dose chemotherapy. Doses of TPO for ex vivo treatment of bone marrow will be in the range of 100 pg/ml to 10 ng/ml, preferably 500 pg/ml to 3 ng/ml. Doses of EPO will be from 0.5 units/ml to 5 units/ml, preferably from 0.5 units/ml to 2 units/ml.

The invention is further illustrated by the following non-limiting examples.

EXAMPLE I

Induction of Red Blood Cell Colony Formation

At physiological levels of EPO, the addition of TPO stimulates the production of erythroid colony forming units (CFU-E) above levels of production seen with EPO alone.

Bone marrow cells were isolated from $BDF_1$ mice (Jackson Labs, Bar Harbor, Me.) by femoral flushing. The cells ($2\times10^4$/100 μg clot) were resuspended in medium containing a medium (Flow Laboratories, McLean, Va.) supplemented with 30% fetal calf serum (Hyclone, Logan, Utah), 1% bovine serum albumin, $5\times10-5$ M b-mercaptoethanol; and $2\times10^{-5}$ M $CaCl_2$. One hundred-twenty U/ml recombinant mouse TPO were added to 1.5% pokeweed mitogen stimulated spleen cell conditioned medium and 2 units/ml of human EPO to promote the growth of early erythroid progenitors (BFU-E). Two units/ml of human EPO was added late erythroid progenitor (CFU-E) colonies.

Units of TPO activity were determined by assaying mitogenic activity on a TPO-dependent cell line. A BHK cell line transfected with a mouse TPO expression vector (pZGmpl-1081; deposited under the terms of the Budapest Treaty with American Type Culture Collection, 12301 Parklawn Drive, Rockville, Md. on Feb. 14, 1994 as an *E. coli* DH5a transformant and assigned accession number 69566) as described in copending U.S. patent application Ser. No. 08/252,491, filed Jun. 1, 1994, was grown in serum-free medium. Conditioned medium was collected, and an asymptotic mitogenic activity curve was generated using this standard solution. The target cells were BaF3/MPLR1.1 (IL-3-dependent cells expressing a stably transfected Type I mouse MPL receptor; deposited on Sep. 28, 1994, under the terms of the Budapest Treaty with American Type Culture Collection, 12301 Parklawn Drive, Rockville, Md. and assigned the accession number CRL 11723). The point of ½ maximal activity (average of 16 curves) was assigned the value of 50 U/ml. The original standard solution was calculated to contain 26,600 U/ml mouse TPO.

For test samples, a culture supernatant or purified protein preparation was diluted in RPMI 1640 medium supplemented with 57 μM 2-mercaptoethanol, 2 mM L-glutamine, 1 mM sodium pyruvate, PSN antibiotic mixture, 10 mM HEPES and 10% heat inactivated fetal bovine serum, generally using 8–24 dilutions. Briefly, 100 μg of diluted test sample or standard sample and 100 μg BaF3 cells (final cell number added about 10,000 cells/well) were combined in wells of a 96 well plate. Internal standards included eight 2-fold dilutions of 100 U/ml mouse TPO for mouse TPO assays, or eight 2-fold dilutions of 150 U/ml mouse TPO for human TPO assays. To each well was added 2 μg $^3$H-thymidine (1 μC/μl; Amersham), and the plates were incubated overnight at 37° C.

The contents of each well of each plate were transferred to a filter/plate using a Packard apparatus. The filters were washed 8 times with water, and the filters were dried and counted. Units of TPO activity in each sample well were determined by comparison to the standard curve.

Human EPO (Amgen Inc., Thousand Oaks, Calif.) was added at varying concentrations in the range from 0 to 300 mUnits/ml with or without 120 units TPO. Clotting was initiated by the addition of 10% citrated bovine plasma.

The bone marrow cultures were incubated for two days at 37° C. in a fully humidified atmosphere containing 5% $CO_2$. Erythroid colonies contained greater than 40 cells. After incubation, the clots were harvested, dried, stained with benzidine and erythroid colonies were counted (Broudy et al. *Arch. of Biochem. and Biophys.* 265:329–336, 1988). The results have been indexed to that of the maximal colony growth and represent the mean of at least three separate experiments of two to three replicate plates.

FIG. 1 shows that at physiological concentrations of EPO, in the range of 0–100 mUnits/ml, the addition of 120 U/ml TPO results in a significant increase the number of erythroid progenitor cell colonies.

EXAMPLE II

TPO-Induced Increase in Reticulocyte Counts

TPO-treated animals have elevated reticulocyte counts when compared to untreated animals.

Ten male BALB/c mice (Simonsen Labs, Gilroy, Calif.; approximately 8 weeks old) were divided into a TPO-treated group of five animals and a sham group of five animals. A 12.5 kU dose of mouse recombinant TPO was prepared in 20 mM Tris (pH 8.1), 0.9% NaCl and 0.25% rabbit serum albumin (RSA). The sham animals were treated with buffer alone. Each animal was given a 0.2 ml intraperitoneal injection once daily with either 12.5 kU TPO or buffer for six consecutive days. On day=0, the animals were bled, and complete blood counts (CBC), including reticulocyte counts, were determined for each animal. On day=6, the animals were bled and sacrificed, and CBCs and reticulocyte counts were measured. For the sham treated animals, the reticulocyte counts went from a baseline at d=0 of 4.5% to 8.7% at d=6, and for the TPO-treated animals, the reticulocyte counts went from a baseline at d=0 of 5.3% to 12.0% at d=6.

EXAMPLE III

Increase in Erythropoiesis in TPO-Treated Animals

TPO administered to animals that had been treated with radiation and a chemotherapeutic drug showed increased erythropoietic recovery when compared to untreated animals.

Four to six-week old, female C57BL/6J mice (Jackson Labs, Bar Harbor, Me.) were irradiated by exposure to $^{137}$Cs using a Gammacell 40 irradiator (Nordion International Inc., Kanata, Ontario, Canada) and treated with 1.2 mg of carboplatin (Bristol Laboratories, Princeton, N.J.) injected intraperitoneally on day=0. The mice were treated either with TPO or TPO buffer only. TPO or TPO buffer was administered on day=1 through day=14. The mice were divided into three groups as follows:

Group 1: 8 mice treated with 500 cGy radiation+1.2 mg carboplatin+TPO buffer for 14 days Group 2: 8 mice treated with 500 cGy radiation+1.2 mg carboplatin+25 kU TPO/day for 14 days Group 3: 8 mice treated with 500 cGY radiation+1.2 mg carboplatin+75 kU TPO/day for 14 days TPO was prepared in a buffer containing 20 mM Tris (pH 8.1), 0.9% NaCl and 0.25% RSA. The mice were bled and CBCs were measured on days 0 (to establish baseline), 4, 6, 8, 10, 11 (CBC and reticulocyte counts), 13 (CBC and reticulocyte counts), 15, 18, 20, 22, 25 and 27 (CBC and reticulocyte counts) and then sacrificed.

Figure 2:
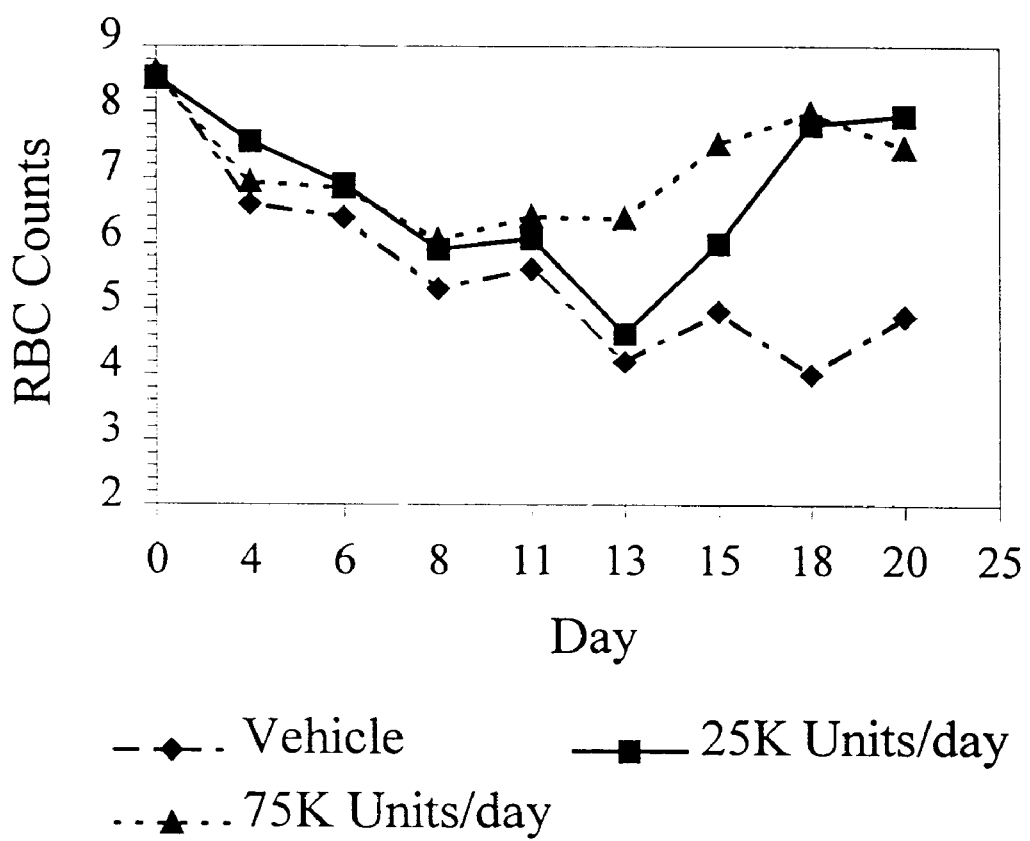
FIG. 2 illustrates that following the addition of TPO to animals made pancytopenic with prior irradiation and chemotherapy, the decline in red blood cell count is not as severe, and returns to normal sooner, in animals given TPQ.

FIG. 2 demonstrates that Group 2 and Group 3, TPO-treated animals, had a statistically shorter period of anemia (their red blood cell levels recovered to baseline significantly faster than animals treated with buffer only).

Table 4 demonstrates that by day 13, Group 2 and Group 3 TPO-treated animals had increased reticulocyte counts relative to the animals treated with buffer only. These data indicate that the improved red blood cell level was due to an increase in red blood cell production rather than a decrease in red blood cell destruction (or loss, i.e. less bleeding). Furthermore, no evidence of pathological bleeding was noted in the control or treatment groups.

TABLE 4

| Dose | Day 10 | Day 13 | Day 15 | Day 27 |
|---|---|---|---|---|
| 75 kU/day | 7.0 ± 1.8 (4) | 9.7 ± 2.2 (4) | 16.9 ± 1.1 (4) | 5.3 ± 0.6 (8) |
| 25 kU/day | 4.6 ± 3.1 (3) | 9.8 ± 1.3 (3) | 10.6 ± 0.9 (3) | 2.7 ± 0.4 (7) |
| vehicle | 4.7 ± 3.3 (3) | 2.4 ± 1.2 (3) | 7.7 ± 4.3 (3) | 3.2 ± 0.9 (6) | mean±SEM (n)

The mean is calculated from percentage of red blood cells that are reticulocytes.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for stimulating erythropoiesis comprising:

determining the hematocrit level in a mammal to be less than 33% of total blood volume, whereby said mammal is identified to be anemic;

administering to said anemic mammal a composition comprising thrombopoietin (TPO) in combination with a pharmaceutically acceptable vehicle wherein the TPO comprises a sequence of amino acids selected from group consisting of:

the sequence of amino acids shown in SEQ ID NO:2 from amino acid residue 1 to residue 172;

the sequence of amino acids shown in SEQ ID NO:2 from amino acid residue 1 to residue 173;

the sequence of amino acids shown in SEQ ID NO:2 from amino acid residue 1 to residue 175;

the sequence of amino acids shown in SEQ ID NO:2 from amino acid residue 1 to amino acid residue 353;

the sequence of amino acids shown in SEQ ID NO:2 from amino acid residue 22 to residue 353;

the sequence of amino acids shown in SEQ ID NO:2 from amino acid residue 22 to residue 172;

the sequence of amino acids shown in SEQ ID NO:2 from amino acid residue 22 to residue 173;

the sequence of amino acids shown in SEQ ID NO:2 from amino acid residue 22 to residue 175;

the sequence of amino acids shown in SEQ ID NO:2 from amino acid residue 28 to residue 172 the sequence of amino acids shown in SEQ ID NO:2 from amino acid residue 28 to residue 173;

the sequence of amino acids shown in SEQ ID NO:2 from amino acid residue 28 to residue 175; and the sequence of amino acids shown in SEQ ID NO:2 from amino acid residue 28 to residue 353;

in an amount sufficient to produce an increase in hematocrit level above 33% of total blood volume; and monitoring the hematocrit level following said administration.

2. The method of claim 1, wherein said mammal has a reticulocyte count of less 0.8%.

3. The method of claim 1, wherein said mammal has been treated with radiation or chemotherapy.

4. The method of claim 1, wherein $1.0 \times 10^5$ to $100 \times 10^5$ units TPO/kg/day is administered to said mammal.

5. The method of claim 1, wherein 1.2 μg/kg/day to 114 μg TPO/kg/day is administered to said mammal.

6. The method of claim 1, for stimulating erythropoiesis comprising administering to a patient in need thereof a composition comprising TPO, in combination with a pharmaceutically acceptable vehicle, in an amount sufficient for increasing reticulocyte counts at least 2-fold over baseline reticulocyte counts.

7. A method for stimulating erythropoiesis comprising:

determining the hemoglobin level in a mammal to be less than 33% of total blood volume, whereby said mammal is identified to be anemic;

administering to said anemic mammal a composition comprising TPO and erythropoietin (EPO) in combination with a pharmaceutically acceptable vehicle wherein the TPO comprises a sequence of amino acids selected from group consisting of:

the sequence of amino acids shown in SEQ ID NO:2 from amino acid residue 1 to residue 172;

the sequence of amino acids shown in SEQ ID NO:2 from amino acid residue 1 to residue 173;

the sequence of amino acids shown in SEQ ID NO:2 from amino acid residue 1 to residue 175;

the sequence of amino acids shown in SEQ ID NO:2 from amino acid residue 1 to amino acid residue 353;

the sequence of amino acids shown in SEQ ID NO:2 from amino acid residue 22 to residue 353;

the sequence of amino acids shown in SEQ ID NO:2 from amino acid residue 22 to residue 172;

the sequence of amino acids shown in SEQ ID NO:2 from amino acid residue 22 to residue 173;

the sequence of amino acids shown in SEQ ID NO:2 from amino acid residue 22 to residue 175;

the sequence of amino acids shown in SEQ ID NO:2 from amino acid residue 28 to residue 172 the sequence of amino acids shown in SEQ ID NO:2 from amino acid residue 28 to residue 173;

the sequence of amino acids shown in SEQ ID NO:2 from amino acid residue 28 to residue 175; and the sequence of amino acids shown in SEQ ID NO:2 from amino acid residue 28 to residue 353;

in an amount sufficient to produce an increase of 33% of total blood volume; and monitoring the hematocrit level following said administration.

8. The method of claim 7, wherein said mammal has a hemoglobin level of less than 11 gm/100 ml of blood.

9. The method of claim 7, wherein said mammal has a reticulocyte count of less than 0.8%.

10. The method of claim 7, wherein said mammal has been treated with radiation or chemotherapy.

11. The method of claim 7, wherein the EPO is human EPO.

12. The method of claim 7, wherein $1.0 \times 10^5$ to $100 \times 10^5$ units TPO/kg/day and 10 to 150 units EPO/kg/day are administered to said mammal.

13. The method of claim 7, wherein 1.2 μg/kq/day to 114 μg TPO/kg/day and 1 to 150 units EPO/kg/day are administered to said mammal.

14. The method of claim 7 for stimulating erythropoiesis comprising administering to a patient in need thereof a composition comprising TPO and EPO, in combination with a pharmaceutically acceptable vehicle, in an amount sufficient for increasing reticulocyte counts at least 2-fold over baseline reticulocyte counts.

* * * * *

UNITED STATES PATENT AND TRADEMARK OFFICE
CERTIFICATE OF CORRECTION

PATENT NO.     : 6,099,830
DATED          : August 8, 2000
INVENTOR(S)    : Kenneth Kaushansky It is certified that error appears in the above-identified patent and that said Letters Patent is hereby corrected as shown below:

<u>Title page,</u>
Item [73], Assignees, please delete "ZymoGenetics, Inc.; University of Washington, both of Seattle, Wash." and insert therefor -- University of Washington, Seattle, Wash. --.

Signed and Sealed this

Fourteenth Day of January, 2003

JAMES E. ROGAN
*Director of the United States Patent and Trademark Office*

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1062 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 1..1059

(xi) SEQUENCE DESCRIPTION: SEQ ID NO:1:

```
ATG GAG CTG ACT GAA TTG CTC CTC GTG GTC ATG CTT CTC CTA ACT GCA        48
Met Glu Leu Thr Glu Leu Leu Leu Val Val Met Leu Leu Leu Thr Ala
  1               5                  10                  15

AGG CTA ACG CTG TCC AGC CCG GCT CCT CCT GCT TGT GAC CTC CGA GTC        96
Arg Leu Thr Leu Ser Ser Pro Ala Pro Pro Ala Cys Asp Leu Arg Val
             20                  25                  30

CTC AGT AAA CTG CTT CGT GAC TCC CAT GTC CTT CAC AGC AGA CTG AGC       144
Leu Ser Lys Leu Leu Arg Asp Ser His Val Leu His Ser Arg Leu Ser
         35                  40                  45

CAG TGC CCA GAG GTT CAC CCT TTG CCT ACA CCT GTC CTG CTG CCT GCT       192
Gln Cys Pro Glu Val His Pro Leu Pro Thr Pro Val Leu Leu Pro Ala
     50                  55                  60

GTG GAC TTT AGC TTG GGA GAA TGG AAA ACC CAG ATG GAG GAG ACC AAG       240
Val Asp Phe Ser Leu Gly Glu Trp Lys Thr Gln Met Glu Glu Thr Lys
 65                  70                  75                  80
```

```
GCA CAG GAC ATT CTG GGA GCA GTG ACC CTT CTG CTG GAG GGA GTG ATG        288
Ala Gln Asp Ile Leu Gly Ala Val Thr Leu Leu Leu Glu Gly Val Met
                85                  90                  95

GCA GCA CGG GGA CAA CTG GGA CCC ACT TGC CTC TCA TCC CTC CTG GGG        336
Ala Ala Arg Gly Gln Leu Gly Pro Thr Cys Leu Ser Ser Leu Leu Gly
            100                 105                 110

CAG CTT TCT GGA CAG GTC CGT CTC CTC CTT GGG GCC CTG CAG AGC CTC        384
Gln Leu Ser Gly Gln Val Arg Leu Leu Leu Gly Ala Leu Gln Ser Leu
        115                 120                 125

CTT GGA ACC CAG CTT CCT CCA CAG GGC AGG ACC ACA GCT CAC AAG GAT        432
Leu Gly Thr Gln Leu Pro Pro Gln Gly Arg Thr Thr Ala His Lys Asp
    130                 135                 140

CCC AAT GCC ATC TTC CTG AGC TTC CAA CAC CTG CTC CGA GGA AAG GTG        480
Pro Asn Ala Ile Phe Leu Ser Phe Gln His Leu Leu Arg Gly Lys Val
145                 150                 155                 160

CGT TTC CTG ATG CTT GTA GGA GGG TCC ACC CTC TGC GTC AGG CGG GCC        528
Arg Phe Leu Met Leu Val Gly Gly Ser Thr Leu Cys Val Arg Arg Ala
                165                 170                 175

CCA CCC ACC ACA GCT GTC CCC AGC AGA ACC TCT CTA GTC CTC ACA CTG        576
Pro Pro Thr Thr Ala Val Pro Ser Arg Thr Ser Leu Val Leu Thr Leu
            180                 185                 190

AAC GAG CTC CCA AAC AGG ACT TCT GGA TTG TTG GAG ACA AAC TTC ACT        624
Asn Glu Leu Pro Asn Arg Thr Ser Gly Leu Leu Glu Thr Asn Phe Thr
        195                 200                 205

GCC TCA GCC AGA ACT ACT GGC TCT GGG CTT CTG AAG TGG CAG CAG GGA        672
Ala Ser Ala Arg Thr Thr Gly Ser Gly Leu Leu Lys Trp Gln Gln Gly
    210                 215                 220

TTC AGA GCC AAG ATT CCT GGT CTG CTG AAC CAA ACC TCC AGG TCC CTG        720
Phe Arg Ala Lys Ile Pro Gly Leu Leu Asn Gln Thr Ser Arg Ser Leu
225                 230                 235                 240

GAC CAA ATC CCC GGA TAC CTG AAC AGG ATA CAC GAA CTC TTG AAT GGA        768
Asp Gln Ile Pro Gly Tyr Leu Asn Arg Ile His Glu Leu Leu Asn Gly
                245                 250                 255

ACT CGT GGA CTC TTT CCT GGA CCC TCA CGC AGG ACC CTA GGA GCC CCG        816
Thr Arg Gly Leu Phe Pro Gly Pro Ser Arg Arg Thr Leu Gly Ala Pro
            260                 265                 270

GAC ATT TCC TCA GGA ACA TCA GAC ACA GGC TCC CTG CCA CCC AAC CTC        864
Asp Ile Ser Ser Gly Thr Ser Asp Thr Gly Ser Leu Pro Pro Asn Leu
        275                 280                 285

CAG CCT GGA TAT TCT CCT TCC CCA ACC CAT CCT CCT ACT GGA CAG TAT        912
Gln Pro Gly Tyr Ser Pro Ser Pro Thr His Pro Pro Thr Gly Gln Tyr
    290                 295                 300

ACG CTC TTC CCT CTT CCA CCC ACC TTG CCC ACC CCT GTG GTC CAG CTC        960
Thr Leu Phe Pro Leu Pro Pro Thr Leu Pro Thr Pro Val Val Gln Leu
305                 310                 315                 320

CAC CCC CTG CTT CCT GAC CCT TCT GCT CCA ACG CCC ACC CCT ACC AGC       1008
His Pro Leu Leu Pro Asp Pro Ser Ala Pro Thr Pro Thr Pro Thr Ser
                325                 330                 335

CCT CTT CTA AAC ACA TCC TAC ACC CAC TCC CAG AAT CTG TCT CAG GAA       1056
Pro Leu Leu Asn Thr Ser Tyr Thr His Ser Gln Asn Leu Ser Gln Glu
            340                 345                 350

GGG TAA                                                                1062
Gly
```

(2) INFORMATION FOR SEQ ID NO:2:

(i) SEQUENCE CHARACTERISTICS:
        (A) LENGTH: 353 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Leu Thr Glu Leu Leu Val Val Met Leu Leu Leu Thr Ala
 1               5                  10                  15

Arg Leu Thr Leu Ser Ser Pro Ala Pro Pro Ala Cys Asp Leu Arg Val
            20                  25                  30

Leu Ser Lys Leu Leu Arg Asp Ser His Val Leu His Ser Arg Leu Ser
        35                  40                  45

Gln Cys Pro Glu Val His Pro Leu Pro Thr Pro Val Leu Leu Pro Ala
    50                  55                  60

Val Asp Phe Ser Leu Gly Glu Trp Lys Thr Gln Met Glu Glu Thr Lys
 65                  70                  75                  80

Ala Gln Asp Ile Leu Gly Ala Val Thr Leu Leu Glu Gly Val Met
                85                  90                  95

Ala Ala Arg Gly Gln Leu Gly Pro Thr Cys Leu Ser Ser Leu Leu Gly
            100                 105                 110

Gln Leu Ser Gly Gln Val Arg Leu Leu Leu Gly Ala Leu Gln Ser Leu
        115                 120                 125

Leu Gly Thr Gln Leu Pro Pro Gln Gly Arg Thr Thr Ala His Lys Asp
130                 135                 140

Pro Asn Ala Ile Phe Leu Ser Phe Gln His Leu Leu Arg Gly Lys Val
145                 150                 155                 160

Arg Phe Leu Met Leu Val Gly Gly Ser Thr Leu Cys Val Arg Arg Ala
                165                 170                 175

Pro Pro Thr Thr Ala Val Pro Ser Arg Thr Ser Leu Val Leu Thr Leu
            180                 185                 190

Asn Glu Leu Pro Asn Arg Thr Ser Gly Leu Leu Glu Thr Asn Phe Thr
        195                 200                 205

Ala Ser Ala Arg Thr Thr Gly Ser Gly Leu Leu Lys Trp Gln Gln Gly
    210                 215                 220

Phe Arg Ala Lys Ile Pro Gly Leu Leu Asn Gln Thr Ser Arg Ser Leu
225                 230                 235                 240

Asp Gln Ile Pro Gly Tyr Leu Asn Arg Ile His Glu Leu Leu Asn Gly
                245                 250                 255

Thr Arg Gly Leu Phe Pro Gly Pro Ser Arg Arg Thr Leu Gly Ala Pro
            260                 265                 270

Asp Ile Ser Ser Gly Thr Ser Asp Thr Gly Ser Leu Pro Pro Asn Leu
        275                 280                 285

Gln Pro Gly Tyr Ser Pro Ser Pro Thr His Pro Pro Thr Gly Gln Tyr
    290                 295                 300

Thr Leu Phe Pro Leu Pro Pro Thr Leu Pro Thr Pro Val Val Gln Leu
305                 310                 315                 320

His Pro Leu Leu Pro Asp Pro Ser Ala Pro Thr Pro Thr Pro Thr Ser
                325                 330                 335

Pro Leu Leu Asn Thr Ser Tyr Thr His Ser Gln Asn Leu Ser Gln Glu
            340                 345                 350

Gly
```

(2) INFORMATION FOR SEQ ID NO:3:

(i) SEQUENCE CHARACTERISTICS:
        (A) LENGTH: 1486 base pairs
        (B) TYPE: nucleic acid

```
            (C) STRANDEDNESS: double
            (D) TOPOLOGY: linear (ii) MOLECULE TYPE: cDNA (vii) IMMEDIATE SOURCE:
             (B) CLONE: 1081

(ix) FEATURE:
             (A) NAME/KEY: CDS
             (B) LOCATION: 105..1241

(xi) SEQUENCE DESCRIPTION: SEQ ID NO:3:

CCTCGTGCCG GTCCTGAGGC CCTTCTCCAC CCGGACAGAG TCCTTGGCCC ACCTCTCTCC           60

CACCCGACTC TGCCGAAAGA AGCACAGAAG CTCAAGCCGC CTCC ATG GCC CCA GGA          116
                                                Met Ala Pro Gly
                                                 1

AAG ATT CAG GGG AGA GGC CCC ATA CAG GGA GCC ACT TCA GTT AGA CAC          164
Lys Ile Gln Gly Arg Gly Pro Ile Gln Gly Ala Thr Ser Val Arg His
 5                  10                  15                  20

CTG GCC AGA ATG GAG CTG ACT GAT TTG CTC CTG GCG GCC ATG CTT CTT          212
Leu Ala Arg Met Glu Leu Thr Asp Leu Leu Leu Ala Ala Met Leu Leu
                 25                  30                  35

GCA GTG GCA AGA CTA ACT CTG TCC AGC CCC GTA GCT CCT GCC TGT GAC          260
Ala Val Ala Arg Leu Thr Leu Ser Ser Pro Val Ala Pro Ala Cys Asp
         40                  45                  50

CCC AGA CTC CTA AAT AAA CTG CTG CGT GAC TCC CAC CTC CTT CAC AGC          308
Pro Arg Leu Leu Asn Lys Leu Leu Arg Asp Ser His Leu Leu His Ser
     55                  60                  65

CGA CTG AGT CAG TGT CCC GAC GTC GAC CCT TTG TCT ATC CCT GTT CTG          356
Arg Leu Ser Gln Cys Pro Asp Val Asp Pro Leu Ser Ile Pro Val Leu
 70                  75                  80

CTG CCT GCT GTG GAC TTT AGC CTG GGA GAA TGG AAA ACC CAG ACG GAA          404
Leu Pro Ala Val Asp Phe Ser Leu Gly Glu Trp Lys Thr Gln Thr Glu
 85                  90                  95                 100

CAG AGC AAG GCA CAG GAC ATT CTA GGG GCA GTG TCC CTT CTA CTG GAG          452
Gln Ser Lys Ala Gln Asp Ile Leu Gly Ala Val Ser Leu Leu Leu Glu
                 105                 110                 115

GGA GTG ATG GCA GCA CGA GGA CAG TTG GAA CCC TCC TGC CTC TCA TCC          500
Gly Val Met Ala Ala Arg Gly Gln Leu Glu Pro Ser Cys Leu Ser Ser
         120                 125                 130

CTC CTG GGA CAG CTT TCT GGG CAG GTT CGC CTC CTC TTG GGG GCC CTG          548
Leu Leu Gly Gln Leu Ser Gly Gln Val Arg Leu Leu Leu Gly Ala Leu
     135                 140                 145

CAG GGC CTC CTA GGA ACC CAG CTT CCT CTA CAG GGC AGG ACC ACA GCT          596
Gln Gly Leu Leu Gly Thr Gln Leu Pro Leu Gln Gly Arg Thr Thr Ala
 150                 155                 160

CAC AAG GAC CCC AAT GCC CTC TTC TTG AGC TTG CAA CAA CTG CTT CGG          644
His Lys Asp Pro Asn Ala Leu Phe Leu Ser Leu Gln Gln Leu Leu Arg
165                 170                 175                 180

GGA AAG GTG CGC TTC CTG CTT CTG GTA GAA GGT CCC ACC CTC TGT GTC          692
Gly Lys Val Arg Phe Leu Leu Leu Val Glu Gly Pro Thr Leu Cys Val
                 185                 190                 195

AGA CGG ACC CTG CCA ACC ACA GCT GTC CCA AGC AGT ACT TCT CAA CTC          740
Arg Arg Thr Leu Pro Thr Thr Ala Val Pro Ser Ser Thr Ser Gln Leu
         200                 205                 210

CTC ACA CTA AAC AAG TTC CCA AAC AGG ACT TCT GGA TTG TTG GAG ACG          788
Leu Thr Leu Asn Lys Phe Pro Asn Arg Thr Ser Gly Leu Leu Glu Thr
     215                 220                 225

AAC TTC AGT GTC ACA GCC AGA ACT GCT GGC CCT GGA CTT CTG AGC AGG          836
Asn Phe Ser Val Thr Ala Arg Thr Ala Gly Pro Gly Leu Leu Ser Arg
 230                 235                 240
```

```
CTT CAG GGA TTC AGA GTC AAG ATT ACT CCT GGT CAG CTA AAT CAA ACC        884
Leu Gln Gly Phe Arg Val Lys Ile Thr Pro Gly Gln Leu Asn Gln Thr
245                 250                 255                 260

TCC AGG TCC CCA GTC CAA ATC TCT GGA TAC CTG AAC AGG ACA CAC GGA        932
Ser Arg Ser Pro Val Gln Ile Ser Gly Tyr Leu Asn Arg Thr His Gly
                265                 270                 275

CCT GTG AAT GGA ACT CAT GGG CTC TTT GCT GGA ACC TCA CTT CAG ACC        980
Pro Val Asn Gly Thr His Gly Leu Phe Ala Gly Thr Ser Leu Gln Thr
            280                 285                 290

CTG GAA GCC TCA GAC ATC TCG CCC GGA GCT TTC AAC AAA GGC TCC CTG       1028
Leu Glu Ala Ser Asp Ile Ser Pro Gly Ala Phe Asn Lys Gly Ser Leu
        295                 300                 305

GCA TTC AAC CTC CAG GGT GGA CTT CCT CCT TCT CCA AGC CTT GCT CCT       1076
Ala Phe Asn Leu Gln Gly Gly Leu Pro Pro Ser Pro Ser Leu Ala Pro
    310                 315                 320

GAT GGA CAC ACA CCC TTC CCT CCT TCA CCT GCC TTG CCC ACC ACC CAT       1124
Asp Gly His Thr Pro Phe Pro Pro Ser Pro Ala Leu Pro Thr Thr His
325                 330                 335                 340

GGA TCT CCA CCC CAG CTC CAC CCC CTG TTT CCT GAC CCT TCC ACC ACC       1172
Gly Ser Pro Pro Gln Leu His Pro Leu Phe Pro Asp Pro Ser Thr Thr
                345                 350                 355

ATG CCT AAC TCT ACC GCC CCT CAT CCA GTC ACA ATG TAC CCT CAT CCC       1220
Met Pro Asn Ser Thr Ala Pro His Pro Val Thr Met Tyr Pro His Pro
            360                 365                 370

AGG AAT TTG TCT CAG GAA ACA TAGCGCGGGC ACTGGCCCAG TGAGCGTCTG          1271
Arg Asn Leu Ser Gln Glu Thr
        375

CAGCTTCTCT CGGGGACAAG CTTCCCCAGG AAGGCTGAGA GGCAGCTGCA TCTGCTCCAG     1331

ATGTTCTGCT TTCACCTAAA AGGCCCTGGG GAAGGGATAC ACAGCACTGG AGATTGTAAA     1391

ATTTTAGGAG CTATTTTTTT TTAACCTATC AGCAATATTC ATCAGAGCAG CTAGCGATCT     1451

TTGGTCTATT TTCGGTATAA ATTTGAAAAT CACTA                               1486

(2) INFORMATION FOR SEQ ID NO:4:

(i) SEQUENCE CHARACTERISTICS:
        (A) LENGTH: 379 amino acids
        (B) TYPE: amino acid
        (D) TOPOLOGY: linear (ii) MOLECULE TYPE: protein (xi) SEQUENCE DESCRIPTION: SEQ ID NO:4:

Met Ala Pro Gly Lys Ile Gln Gly Arg Gly Pro Ile Gln Gly Ala Thr
1               5                   10                  15

Ser Val Arg His Leu Ala Arg Met Glu Leu Thr Asp Leu Leu Leu Ala
                20                  25                  30

Ala Met Leu Leu Ala Val Ala Arg Leu Thr Leu Ser Ser Pro Val Ala
            35                  40                  45

Pro Ala Cys Asp Pro Arg Leu Leu Asn Lys Leu Leu Arg Asp Ser His
        50                  55                  60

Leu Leu His Ser Arg Leu Ser Gln Cys Pro Asp Val Asp Pro Leu Ser
65                  70                  75                  80

Ile Pro Val Leu Leu Pro Ala Val Asp Phe Ser Leu Gly Glu Trp Lys
                85                  90                  95

Thr Gln Thr Glu Gln Ser Lys Ala Gln Asp Ile Leu Gly Ala Val Ser
                100                 105                 110

Leu Leu Leu Glu Gly Val Met Ala Ala Arg Gly Gln Leu Glu Pro Ser
```

```
                    115                 120                 125
Cys Leu Ser Ser Leu Leu Gly Gln Leu Ser Gly Gln Val Arg Leu Leu
    130                 135                 140

Leu Gly Ala Leu Gln Gly Leu Leu Gly Thr Gln Leu Pro Leu Gln Gly
145                 150                 155                 160

Arg Thr Thr Ala His Lys Asp Pro Asn Ala Leu Phe Leu Ser Leu Gln
                165                 170                 175

Gln Leu Leu Arg Gly Lys Val Arg Phe Leu Leu Val Glu Gly Pro
                180                 185                 190

Thr Leu Cys Val Arg Arg Thr Leu Pro Thr Thr Ala Val Pro Ser Ser
        195                 200                 205

Thr Ser Gln Leu Leu Thr Leu Asn Lys Phe Pro Asn Arg Thr Ser Gly
    210                 215                 220

Leu Leu Glu Thr Asn Phe Ser Val Thr Ala Arg Thr Ala Gly Pro Gly
225                 230                 235                 240

Leu Leu Ser Arg Leu Gln Gly Phe Arg Val Lys Ile Thr Pro Gly Gln
                245                 250                 255

Leu Asn Gln Thr Ser Arg Ser Pro Val Gln Ile Ser Gly Tyr Leu Asn
                260                 265                 270

Arg Thr His Gly Pro Val Asn Gly Thr His Gly Leu Phe Ala Gly Thr
            275                 280                 285

Ser Leu Gln Thr Leu Glu Ala Ser Asp Ile Ser Pro Gly Ala Phe Asn
    290                 295                 300

Lys Gly Ser Leu Ala Phe Asn Leu Gln Gly Gly Leu Pro Pro Ser Pro
305                 310                 315                 320

Ser Leu Ala Pro Asp Gly His Thr Pro Phe Pro Ser Pro Ala Leu
                325                 330                 335

Pro Thr Thr His Gly Ser Pro Pro Gln Leu His Pro Leu Phe Pro Asp
            340                 345                 350

Pro Ser Thr Thr Met Pro Asn Ser Thr Ala Pro His Pro Val Thr Met
        355                 360                 365

Tyr Pro His Pro Arg Asn Leu Ser Gln Glu Thr
    370                 375

(2) INFORMATION FOR SEQ ID NO:5:

(i) SEQUENCE CHARACTERISTICS:
        (A) LENGTH: 4823 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: join(632..644, 876..1003, 1290..1376,
            3309..3476, 3713..4375)

(xi) SEQUENCE DESCRIPTION: SEQ ID NO:5:

CTTTCTTGCT TCTTTCTTT CTTTCTTTCT TTCTTTTTTT TTTTTGAGAC GGAGTTTCAC     60

TCTTATTGCC CAGGCTGGAG TGCAATGGTG CGATCTCGGC TCACCACAAC CTCCGCCTCC   120

CAGGTACAAG CGATTCTCCT GTCTCAGCCT CCCAAGTAGC TTGGATTACA GGCATGAACC   180

ACCACACCCT GCTAGTTTTT TTGTATTTCG TAGAGCCGGG GTTTCACCAT GTTAGTGAGG   240

CTGGTGGCGA ACTCCTGACC TCAGGTGATC CACCCGCCTT GGACTCCCAA AGTGCTGGGA   300

TTACAGGCAT GAGCCACTGC ACCCGGCACA CCATATGCTT TCATCACAAG AAAATGTGAG   360
```

```
AGAATTCAGG GCTTTGGCAG TTCCAGGCTG GTCAGCATCT CAAGCCCTCC CCAGCATCTG    420

TTCACCCTGC CAGGCAGTCT CTTCCTAGAA ACTTGGTTAA ATGTTCACTC TTCTTGCTAC    480

TTTCAGGATA GATTCTTCAC CCTTGGTCCG CCTTTGCCCC ACCCTACTCT GCCCAGAAGT    540

GCAAGAGCCT AAGCCGCCTC CATGGCCCCA GGAAGGATTC AGGGGAGAGG CCCCAAACAG    600

GGAGCCACGC CAGCCAGACA CCCCGGCCAG A ATG GAG CTG ACT  G GTGAGAACAC    654
                                 Met Glu Leu Thr
                                  1

ACCTGAGGGG CTAGGGCCAT ATGGAAACAT GACAGAAGGG GAGAGAGAAA GGAGACACGC    714

TGCAGGGGGC AGGAAGCTGG GGGAACCCAT TCTCCCAAAA ATAAGGGGTC TGAGGGGTGG    774

ATTCCCTGGG TTTCAGGTCT GGGTCCTGAA TGGGAATTCC TGGAATACCA GCTGACAATG    834

ATTTCCTCCT CATCTTTCAA CCTCACCTCT CCTCATCTAA G  AA TTG CTC CTC        886
                                             Glu Leu Leu Leu
                                              5

GTG GTC ATG CTT CTC CTA ACT GCA AGG CTA ACG CTG TCC AGC CCG GCT      934
Val Val Met Leu Leu Leu Thr Ala Arg Leu Thr Leu Ser Ser Pro Ala
 10              15                  20

CCT CCT GCT TGT GAC CTC CGA GTC CTC AGT AAA CTG CTT CGT GAC TCC      982
Pro Pro Ala Cys Asp Leu Arg Val Leu Ser Lys Leu Leu Arg Asp Ser
 25              30                  35                  40

CAT GTC CTT CAC AGC AGA CTG GTGAGAACTC CCAACATTAT CCCCTTTATC        1033
His Val Leu His Ser Arg Leu
             45

CGCGTAACTG GTAAGACACC CATACTCCCA GGAAGACACC ATCACTTCCT CTAACTCCTT   1093

GACCCAATGA CTATTCTTCC CATATTGTCC CCACCTACTG ATCACACTCT CTGACAAGGA   1153

TTATTCTTCA CAATACAGCC CGCATTTAAA AGCTCTCGTC TAGAGATAGT ACTCATGGAG   1213

GACTAGCCTG CTTATTAGGC TACCATAGCT CTCTCTATTT CAGCTCCCTT CTCCCCCCAC   1273

CAATCTTTTT CAACAG AGC CAG TGC CCA GAG GTT CAC CCT TTG CCT ACA       1322
               Ser Gln Cys Pro Glu Val His Pro Leu Pro Thr
                50                  55

CCT GTC CTG CTG CCT GCT GTG GAC TTT AGC TTG GGA GAA TGG AAA ACC     1370
Pro Val Leu Leu Pro Ala Val Asp Phe Ser Leu Gly Glu Trp Lys Thr
 60                  65                  70

CAG ATG GTAAGAAAGC CATCCCTAAC CTTGGCTTCC CTAAGTCCTG TCTTCAGTTT      1426
Gln Met
 75

CCCACTGCTT CCCATGGATT CTCCAACATT CTTGAGCTTT TTAAAAATAT CTCACCTTCA   1486

GCTTGGCCAC CCTAACCCAA TCTACATTCA CCTATGATGA TAGCCTGTGG ATAAGATGAT   1546

GGCTTGCAGG TCCAATATGT GAATAGATTT GAAGCTGAAC ACCATGAAAA GCTGGAGAGA   1606

AATCGCTCAT GGCCATGCCT TTGACCTATT CCCGTTCAGT CTTCTTAAAT TGGCATGAAG   1666

AAGCAAGACT CATATGTCAT CCACAGATGA CACAAAGCTG GGAAGTACCA CTAAAATAAC   1726

AAAAGACTGA ATCAAGATTC AAATCACTGA AAGACTAGGT CAAAAACAAG GTGAAACAAC   1786

AGAGATATAA ACTTCTACAT GTGGGCCGGG GGCTCACGCC TGTAATCCCA GCACTTTGGG   1846

AGGCCGAGGC AGGCAGATCA CCTGAGGGCA GGAGTTTGAG AGCAGCCTGG CCAACATGGC   1906

GAAACCCCGT CTCTACTAAG AATACAGAAT TAGCCGGGCA TGGTAGTGCA TGCCTGTAAT   1966

CCCAGCTACT TGGAAGGCTG AAGCAGGAGA ATCCCTTGAA CCCAGGAGGT GGAGGTTGTA   2026

GTGAGCTGAG ATCATGCCAA TGCACTCCAG CCTGGGTGAC AAGAGCAAAA CTCCGTCTCA   2086

AAAAGAAAAA AAAATTCTAC ATGTGTAAAT TAATGAGTAA AGTCCTATTC CAGCTTTCAG   2146
```

```
                                                          -continued

GCCACAATGC CCTGCTTCCA TCATTTAAGC CTCTGGCCCT AGCACTTCCT ACGAAAAGGA       2206

TCTGAGAGAA TTAAATTGCC CCCAAACTTA CCATGTAACA TTACTGAAGC TGCTATTCTT       2266

AAAGCTAGTA ATTCTTGTCT GTTTGATGTT TAGCATCCCC ATTGTGGAAA TGCTCGTACA       2326

GAACTCTATT CCGAGTGGAC TACACTTAAA TATACTGGCC TGAACACCGG ACATCCCCCT       2386

GAAGACATAT GCTAATTTAT TAAGAGGGAC ATATTAAAC TAACATGTGT CTAGAAAGCA        2446

GCAGCCTGAA CAGAAAGAGA CTAGAAGCAT GTTTTATGGG CAATAGTTTA AAAAACTAAA       2506

ATCTATCCTC AAGAACCCTA GCGTCCCTTC TTCCTTCAGG ACTGAGTCAG GAAGAAGGG        2566

CAGTTCCTAT GGGTCCCTTC TAGTCCTTTC TTTTCATCCT TATGATCATT ATGGTAGAGT      2626

CTCATACCTA CATTTAGTTT ATTTATTATT ATTATTTGAG ACGGAGTCTC ACTCTATCCC       2686

CCAGGCTGGA GTGCAGTGGC ATGATCTCAA CTCACTGCAA CCTCAGCCTC CCGGATTCAA       2746

GCGATTCTCC TGTCTCAGTC TCCCAAGTAG CTGGGATTAC AGGTGCCCAC ACCATGCCC       2806

AGCTAATTTG TGTATTTGTG GTAGAGATGG GGTTTCACCA TGTTGGGCAG GCTGATCTTG       2866

AACTCCTGAC CTCAGGTGAT CCACCTGCCT CAGCCTCCCA AAGTGCTGGG ATTACAGGCG      2926

TGAGCCACTG CACCCAGCCT TCATTCAGTT TAAAAATCAA ATGATCCTAA GGTTTTGCAG       2986

CAGAAAGAGT AAATTTGCAG CACTAGAACC AAGAGGTAAA AGCTGTAACA GGGCAGATTT       3046

CAGCAACGTA AGAAAAAAGG AGCTCTTCTC ACTGAAACCA AGTGTAAGAC CAGGCTGGAC       3106

TAGAGGACAC GGGAGTTTTT GAAGCAGAGG CTGATGACCA GCTGTCGGGA GACTGTGAAG       3166

GAATTCCTGC CCTGGGTGGG ACCTTGGTCC TGTCCAGTTC TCAGCCTGTA TGATTCACTC       3226

TGCTGGCTAC TCCTAAGGCT CCCCACCCGC TTTTAGTGTG CCCTTTGAGG CAGTGCGCTT       3286

CTCTCTTCCA TCTCTTTCTC AG GAG GAG ACC AAG GCA CAG GAC ATT CTG GGA       3338
                         Glu Glu Thr Lys Ala Gln Asp Ile Leu Gly
                                          80                85

GCA GTG ACC CTT CTG CTG GAG GGA GTG ATG GCA GCA CGG GGA CAA CTG        3386
Ala Val Thr Leu Leu Leu Glu Gly Val Met Ala Ala Arg Gly Gln Leu
                 90                  95                 100

GGA CCC ACT TGC CTC TCA TCC CTC CTG GGG CAG CTT TCT GGA CAG GTC        3434
Gly Pro Thr Cys Leu Ser Ser Leu Leu Gly Gln Leu Ser Gly Gln Val
            105                 110                 115

CGT CTC CTC CTT GGG GCC CTG CAG AGC CTC CTT GGA ACC CAG                3476
Arg Leu Leu Leu Gly Ala Leu Gln Ser Leu Leu Gly Thr Gln
        120                 125                 130

GTAAGTCCCC AGTCAAGGGA TCTGTAGAAA CTGTTCTTTT CTGACTCAGT CCCCCTAGAA      3536

GACCTGAGGG AAGAAGGGCT CTTCCAGGGA GCTCAAGGGC AGAAGAGCTG ATCTACTAAG      3596

AGTGCTCCCT GCCAGCCACA ATGCCTGGGT ACTGGCATCC TGTCTTTCCT ACTTAGACAA      3656

GGGAGGCCTG AGATCTGGCC CTGGTGTTTG GCCTCAGGAC CATCCTCTGC CCTCAG          3712

CTT CCT CCA CAG GGC AGG ACC ACA GCT CAC AAG GAT CCC AAT GCC ATC        3760
Leu Pro Pro Gln Gly Arg Thr Thr Ala His Lys Asp Pro Asn Ala Ile
        135                 140                 145

TTC CTG AGC TTC CAA CAC CTG CTC CGA GGA AAG GTG CGT TTC CTG ATG        3808
Phe Leu Ser Phe Gln His Leu Leu Arg Gly Lys Val Arg Phe Leu Met
    150                 155                 160

CTT GTA GGA GGG TCC ACC CTC TGC GTC AGG CGG GCC CCA CCC ACC ACA        3856
Leu Val Gly Gly Ser Thr Leu Cys Val Arg Arg Ala Pro Pro Thr Thr
165                 170                 175                 180

GCT GTC CCC AGC AGA ACC TCT CTA GTC CTC ACA CTG AAC GAG CTC CCA        3904
Ala Val Pro Ser Arg Thr Ser Leu Val Leu Thr Leu Asn Glu Leu Pro
                185                 190                 195

AAC AGG ACT TCT GGA TTG TTG GAG ACA AAC TTC ACT GCC TCA GCC AGA        3952
```

```
Asn Arg Thr Ser Gly Leu Leu Glu Thr Asn Phe Thr Ala Ser Ala Arg
            200                 205                 210

ACT ACT GGC TCT GGG CTT CTG AAG TGG CAG CAG GGA TTC AGA GCC AAG         4000
Thr Thr Gly Ser Gly Leu Leu Lys Trp Gln Gln Gly Phe Arg Ala Lys
            215                 220                 225

ATT CCT GGT CTG CTG AAC CAA ACC TCC AGG TCC CTG GAC CAA ATC CCC         4048
Ile Pro Gly Leu Leu Asn Gln Thr Ser Arg Ser Leu Asp Gln Ile Pro
        230                 235                 240

GGA TAC CTG AAC AGG ATA CAC GAA CTC TTG AAT GGA ACT CGT GGA CTC         4096
Gly Tyr Leu Asn Arg Ile His Glu Leu Leu Asn Gly Thr Arg Gly Leu
245                 250                 255                 260

TTT CCT GGA CCC TCA CGC AGG ACC CTA GGA GCC CCG GAC ATT TCC TCA         4144
Phe Pro Gly Pro Ser Arg Arg Thr Leu Gly Ala Pro Asp Ile Ser Ser
                265                 270                 275

GGA ACA TCA GAC ACA GGC TCC CTG CCA CCC AAC CTC CAG CCT GGA TAT         4192
Gly Thr Ser Asp Thr Gly Ser Leu Pro Pro Asn Leu Gln Pro Gly Tyr
            280                 285                 290

TCT CCT TCC CCA ACC CAT CCT CCT ACT GGA CAG TAT ACG CTC TTC CCT         4240
Ser Pro Ser Pro Thr His Pro Pro Thr Gly Gln Tyr Thr Leu Phe Pro
            295                 300                 305

CTT CCA CCC ACC TTG CCC ACC CCT GTG GTC CAG CTC CAC CCC CTG CTT         4288
Leu Pro Pro Thr Leu Pro Thr Pro Val Val Gln Leu His Pro Leu Leu
        310                 315                 320

CCT GAC CCT TCT GCT CCA ACG CCC ACC CCT ACC AGC CCT CTT CTA AAC         4336
Pro Asp Pro Ser Ala Pro Thr Pro Thr Pro Thr Ser Pro Leu Leu Asn
325                 330                 335                 340

ACA TCC TAC ACC CAC TCC CAG AAT CTG TCT CAG GAA GGG TAAGGTTCTC          4385
Thr Ser Tyr Thr His Ser Gln Asn Leu Ser Gln Glu Gly
                345                 350

AGACACTGCC GACATCAGCA TTGTCTCGTG TACAGCTCCC TTCCCTGCAG GGCGCCCCTG       4445

GGAGACAACT GGACAAGATT TCCTACTTTC TCCTGAAACC CAAAGCCCTG GTAAAAGGGA       4505

TACACAGGAC TGAAAAGGGA ATCATTTTTC ACTGTACATT ATAAACCTTC AGAAGCTATT       4565

TTTTAAGCT ATCAGCAATA CTCATCGAG CAGCTAGCTC TTTGGTCTAT TTTCTGCAGA         4625

AATTTGCAAC TCACTGATTC TCAACATGCT CTTTTTCTGT GATAACTCTG CAAAGACCTG      4685

GGCTGGCCTG GCAGTTGAAC AGAGGGAGAG ACTAACCTTG AGTCAGAAAA CAGAGGAAGG      4745

GTAATTTCCT TTGCTTCAAA TTCAAGGCCT TCCAACGCCC CCATCCCCTT TACTATCATT     4805

CTCAGTGGGA CTCTGATC                                                     4823

(2) INFORMATION FOR SEQ ID NO:6:

(i) SEQUENCE CHARACTERISTICS:
        (A) LENGTH: 353 amino acids
        (B) TYPE: amino acid
        (D) TOPOLOGY: linear (ii) MOLECULE TYPE: protein (xi) SEQUENCE DESCRIPTION: SEQ ID NO:6:

Met Glu Leu Thr Glu Leu Leu Val Val Met Leu Leu Leu Thr Ala
1               5                   10                  15

Arg Leu Thr Leu Ser Ser Pro Ala Pro Pro Ala Cys Asp Leu Arg Val
            20                  25                  30

Leu Ser Lys Leu Leu Arg Asp Ser His Val Leu His Ser Arg Leu Ser
        35                  40                  45

Gln Cys Pro Glu Val His Pro Leu Pro Thr Pro Val Leu Leu Pro Ala
    50                  55                  60
```

-continued

```
Val Asp Phe Ser Leu Gly Glu Trp Lys Thr Gln Met Glu Glu Thr Lys
 65              70                  75                  80

Ala Gln Asp Ile Leu Gly Ala Val Thr Leu Leu Glu Gly Val Met
             85                  90                  95

Ala Ala Arg Gly Gln Leu Gly Pro Thr Cys Leu Ser Ser Leu Leu Gly
            100                 105                 110

Gln Leu Ser Gly Gln Val Arg Leu Leu Leu Gly Ala Leu Gln Ser Leu
            115                 120                 125

Leu Gly Thr Gln Leu Pro Pro Gln Gly Arg Thr Thr Ala His Lys Asp
            130                 135                 140

Pro Asn Ala Ile Phe Leu Ser Phe Gln His Leu Leu Arg Gly Lys Val
145                 150                 155                 160

Arg Phe Leu Met Leu Val Gly Gly Ser Thr Leu Cys Val Arg Arg Ala
                165                 170                 175

Pro Pro Thr Thr Ala Val Pro Ser Arg Thr Ser Leu Val Leu Thr Leu
            180                 185                 190

Asn Glu Leu Pro Asn Arg Thr Ser Gly Leu Leu Glu Thr Asn Phe Thr
            195                 200                 205

Ala Ser Ala Arg Thr Thr Gly Ser Gly Leu Leu Lys Trp Gln Gln Gly
210                 215                 220

Phe Arg Ala Lys Ile Pro Gly Leu Leu Asn Gln Thr Ser Arg Ser Leu
225                 230                 235                 240

Asp Gln Ile Pro Gly Tyr Leu Asn Arg Ile His Glu Leu Leu Asn Gly
            245                 250                 255

Thr Arg Gly Leu Phe Pro Gly Pro Ser Arg Arg Thr Leu Gly Ala Pro
            260                 265                 270

Asp Ile Ser Ser Gly Thr Ser Asp Thr Gly Ser Leu Pro Pro Asn Leu
            275                 280                 285

Gln Pro Gly Tyr Ser Pro Ser Pro Thr His Pro Pro Thr Gly Gln Tyr
            290                 295                 300

Thr Leu Phe Pro Leu Pro Pro Thr Leu Pro Thr Pro Val Val Gln Leu
305                 310                 315                 320

His Pro Leu Leu Pro Asp Pro Ser Ala Pro Thr Pro Thr Pro Thr Ser
            325                 330                 335

Pro Leu Leu Asn Thr Ser Tyr Thr His Ser Gln Asn Leu Ser Gln Glu
            340                 345                 350

Gly
```